(12) United States Patent
Berme et al.

(10) Patent No.: US 8,315,823 B2
(45) Date of Patent: *Nov. 20, 2012

(54) FORCE AND/OR MOTION MEASUREMENT SYSTEM HAVING INERTIAL COMPENSATION AND METHOD THEREOF

(75) Inventors: Necip Berme, Worthington, OH (US); Hasan Cenk Guler, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 52 days.

This patent is subject to a terminal disclaimer.

(21) Appl. No.: 13/173,084

(22) Filed: Jun. 30, 2011

(65) Prior Publication Data

US 2012/0266648 A1    Oct. 25, 2012

Related U.S. Application Data

(63) Continuation-in-part of application No. 13/091,060, filed on Apr. 20, 2011.

(51) Int. Cl.
*G01G 23/01*    (2006.01)
(52) U.S. Cl. ............. 702/41; 702/87; 702/101; 702/173
(58) Field of Classification Search .................... 702/41, 702/42, 87, 101, 102, 174, 173; 600/592
See application file for complete search history.

(56) References Cited

U.S. PATENT DOCUMENTS

| | | | | |
|---|---|---|---|---|
| 3,890,958 | A | * | 6/1975 | Fister et al. .................... 600/527 |
| 4,283,764 | A | | 8/1981 | Crum et al. |
| 4,548,289 | A | * | 10/1985 | Mechling ....................... 600/587 |
| 4,830,021 | A | * | 5/1989 | Thornton ....................... 600/520 |
| 4,991,446 | A | | 2/1991 | Bechtel |
| 5,009,111 | A | | 4/1991 | West et al. |
| 5,488,203 | A | | 1/1996 | Hassel et al. |
| 5,562,572 | A | | 10/1996 | Carmein |
| 5,563,632 | A | | 10/1996 | Roberts |

(Continued)

FOREIGN PATENT DOCUMENTS

CA    2018618 C    4/1991

(Continued)

OTHER PUBLICATIONS

Yang, Feng et al., Correction of the Inertial Effect Resulting From a Plate Moving Under Low Friction Conditions, Journal of Biomechanics, Sep. 2007, vol. 40, Issue 12, pp. 2723-2730.*

(Continued)

*Primary Examiner* — Jeffrey R West
(74) *Attorney, Agent, or Firm* — The Law Office of Patrick F. O'Reilly III, LLC

(57) ABSTRACT

According to one aspect of the invention, a force measurement system includes a force measurement assembly, a motion base configured to displace the force measurement assembly, and an inertial compensation system configured to determine the inertial forces and/or moments resulting from the displacement of the force measurement assembly by the motion base. According to another aspect of the invention, a method for accurately determining the forces and/or moments applied to a surface of a force measurement device by a subject disposed thereon is disclosed, which includes the step of determining, by using an inertial compensation system, the inertial forces and/or moments resulting from the displacement of a force measurement assembly by a motion base. According to still another aspect of the invention, a force and/or motion measurement system having inertial compensation includes a motion acquisition system having a plurality of motion sensing devices configured to capture a subject's movement.

18 Claims, 13 Drawing Sheets

U.S. PATENT DOCUMENTS

| | | | |
|---|---|---|---|
| 5,750,937 A * | 5/1998 | Johnson et al. | 177/25.11 |
| 6,038,488 A | 3/2000 | Barnes et al. | |
| 6,052,114 A | 4/2000 | Morifuji | |
| 6,098,025 A * | 8/2000 | Bae | 702/94 |
| 6,113,237 A | 9/2000 | Ober et al. | |
| 6,152,564 A | 11/2000 | Ober et al. | |
| 6,162,189 A | 12/2000 | Girone et al. | |
| 6,285,358 B1 | 9/2001 | Roberts | |
| 6,295,878 B1 | 10/2001 | Berme | |
| 6,354,155 B1 | 3/2002 | Berme | |
| 6,389,883 B1 | 5/2002 | Berme et al. | |
| 6,508,132 B1 | 1/2003 | Lohr et al. | |
| 6,645,126 B1 | 11/2003 | Martin et al. | |
| 6,736,018 B2 | 5/2004 | Terada | |
| 6,738,065 B1 | 5/2004 | Even-Zohar | |
| 6,774,885 B1 * | 8/2004 | Even-Zohar | 345/156 |
| 6,836,744 B1 | 12/2004 | Asphahani et al. | |
| 6,936,016 B2 | 8/2005 | Berme et al. | |
| 7,102,621 B2 * | 9/2006 | Roberts | 345/173 |
| 7,331,209 B2 | 2/2008 | Saari et al. | |
| 7,931,604 B2 | 4/2011 | Even-Zohar et al. | |
| 7,955,279 B2 * | 6/2011 | Berthonnaud et al. | 600/595 |
| 8,181,541 B2 | 5/2012 | Berme | |
| 2008/0221487 A1 | 9/2008 | Even-Zohar et al. | |
| 2008/0228110 A1 * | 9/2008 | Berme | 600/595 |
| 2010/0013768 A1 | 1/2010 | Leung | |
| 2010/0131113 A1 | 5/2010 | Even-Zohar | |
| 2011/0277562 A1 | 11/2011 | Berme | |

FOREIGN PATENT DOCUMENTS

| | | |
|---|---|---|
| CA | 2160850 C | 6/1996 |
| CA | 2345013 C | 9/2009 |
| JP | 01303296 A | 12/1989 |
| WO | 0106208 A1 | 1/2001 |

OTHER PUBLICATIONS

Pagnacco, Guido et al., Inertially Compensated Force Plate: A Means for Quantifying Subject's Ground Reaction Forces In Non-Inertial Conditions, Biomedical Sciences Instrumentation, 2000, vol. 36, pp. 397-402.*

Robinson, "Design, Control, and Characterization of a Sliding Linear Investigative Platform for Analyzing Lower Limb Stability (SLIP-FALLS)", IEEE Transactions on Rehabilitation Engineering, vol. 6, No. 3, Sep. 1998.*

Dixon, Michael J., Development of a Load-cell Compensation System, Experimental Mechanics, Mar. 1991, pp. 21-24.

Preuss, R. et al., A simple method to estimate force plate inertial components in a moving surface, Journal of Biomechanics, Aug. 2004, vol. 37, Issue 8, pp. 1177-1180.

First office action on the merits (Non-Final Rejection) in U.S. Appl. No. 13/091,060, mailed on Aug. 8, 2011.

Second office action on the merits (Final Rejection) in U.S. Appl. No. 13/091,060 mailed on Oct. 18, 2011.

Third office action on the merits (Non-Final Rejection) in U.S. Appl. No. 13/091,060, mailed on Jun. 22, 2012.

* cited by examiner

Front View

Side View

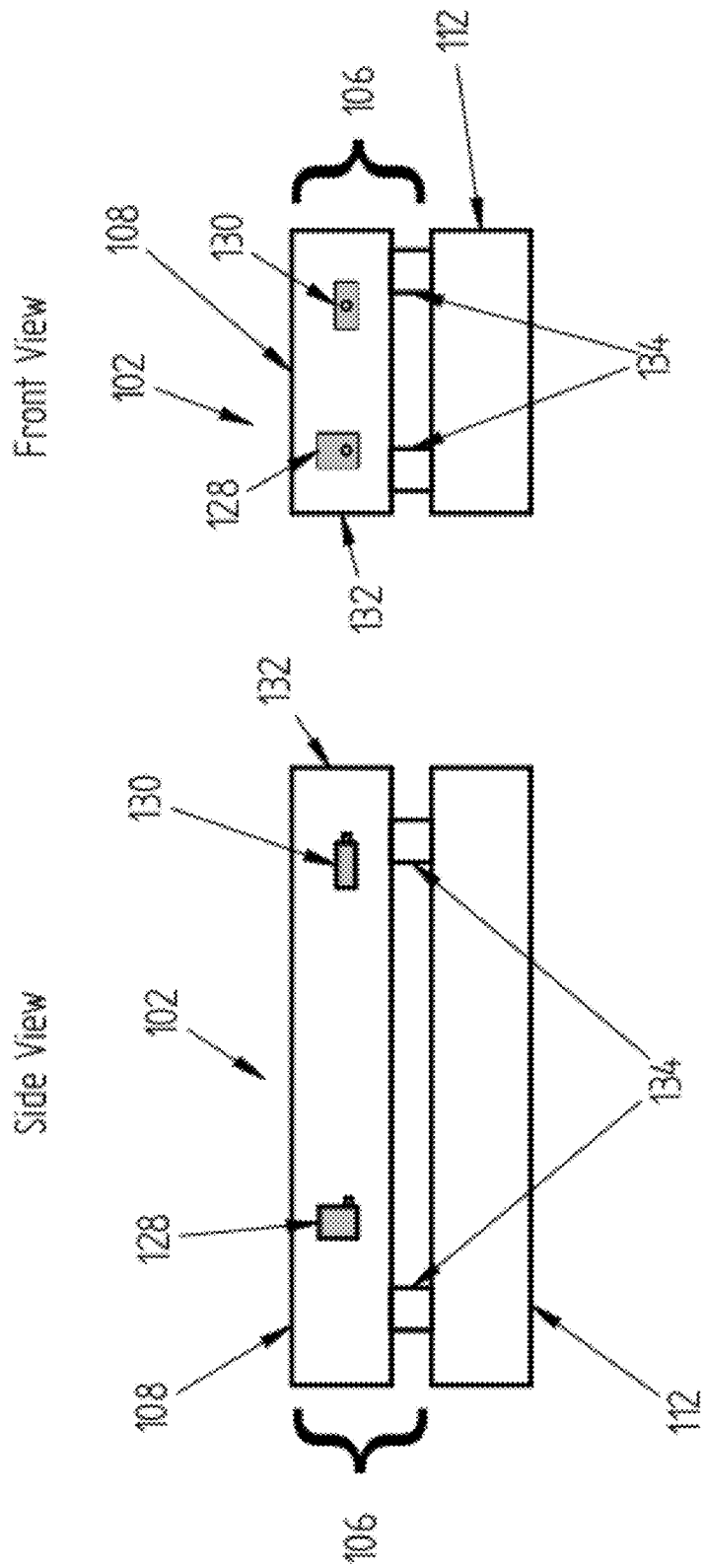

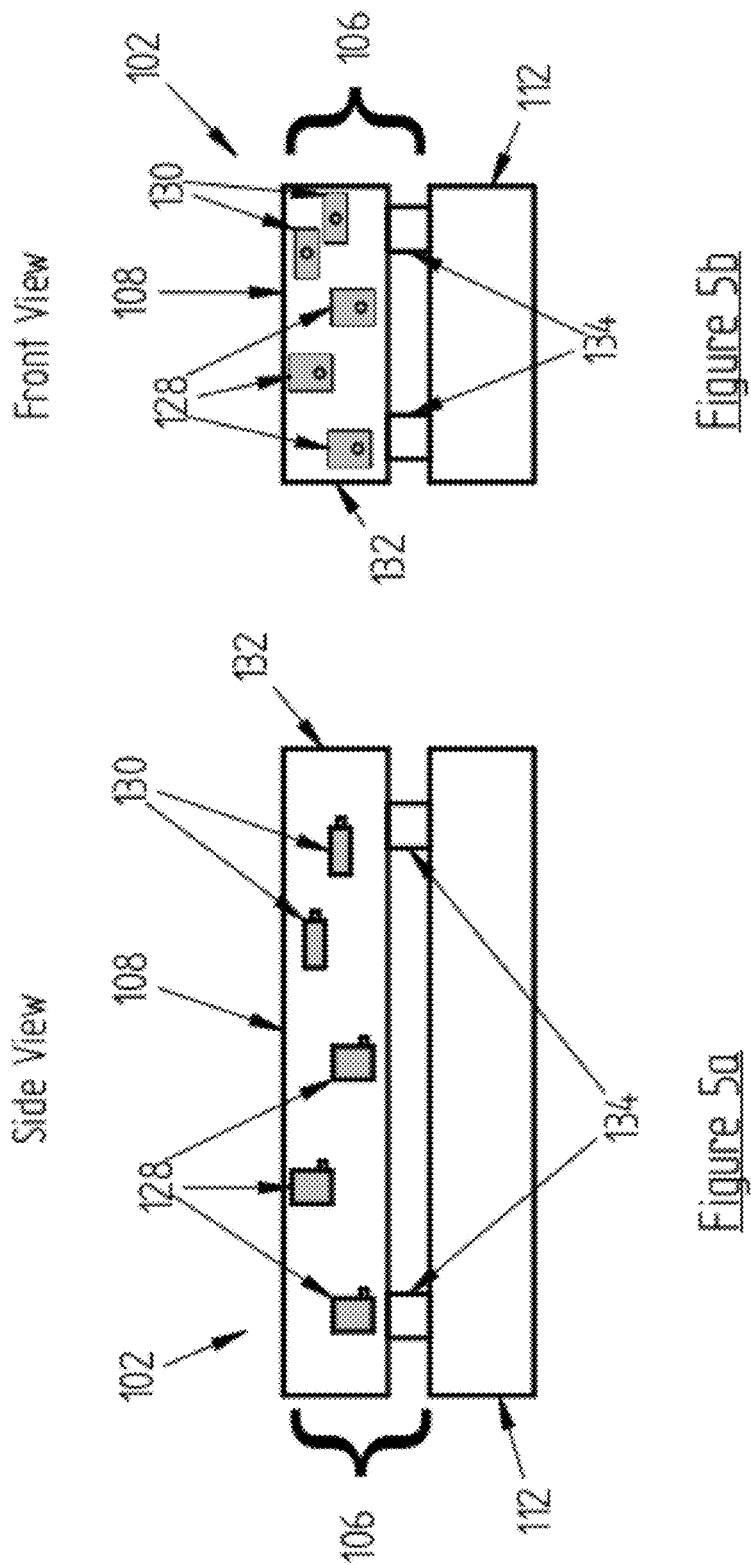

Front View

Side View

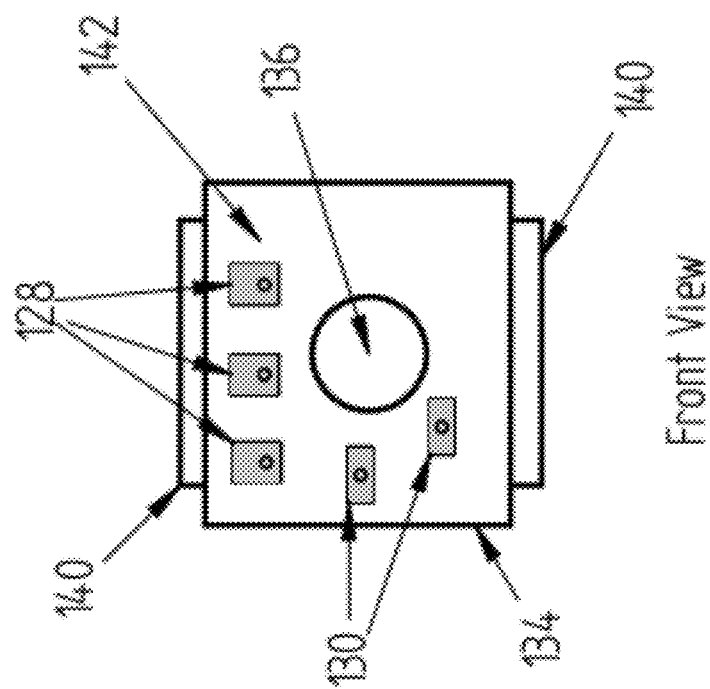
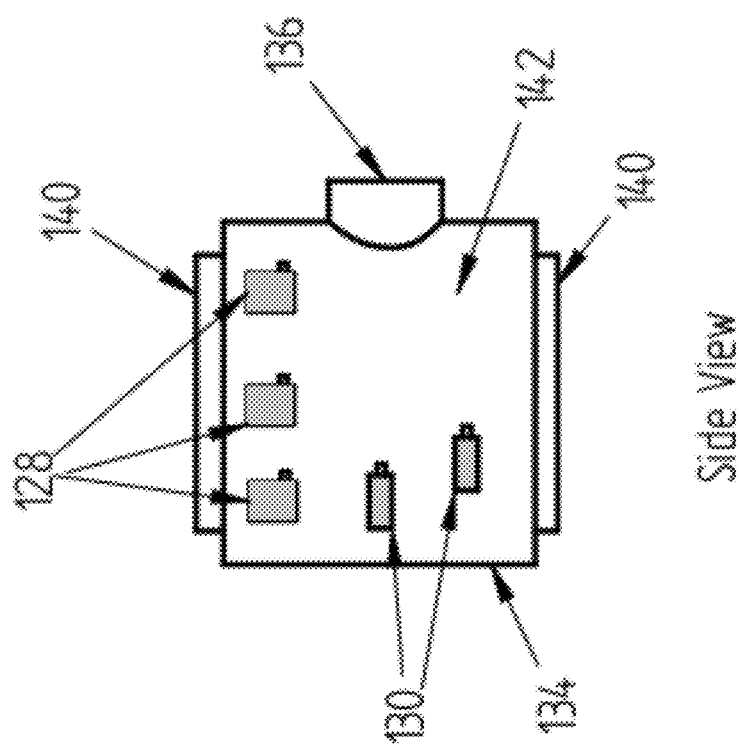

FORCE AND/OR MOTION MEASUREMENT SYSTEM HAVING INERTIAL COMPENSATION AND METHOD THEREOF

CROSS-REFERENCE TO RELATED APPLICATIONS

This patent application is a continuation-in-part application, which is co-pending with, and claims priority from, U.S. Non-Provisional patent application Ser. No. 13/091,060, entitled "Force Measurement System Having Inertial Compensation", filed on Apr. 20, 2011, which is incorporated by reference herein in its entirety by this reference thereto.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to force and/or motion measurement systems. More particularly, the invention relates to force and/or motion measurement systems with inertial compensation.

2. Background and Description of Related Art

Force measurement systems are utilized in various fields to quantify the reaction forces and moments exchanged between a body and support surface. For example, in biomedical applications, force measurement systems are used for gait analysis, assessing balance and mobility, evaluating sports performance, and assessing ergonomics. In order to quantify the forces and moments resulting from the body disposed thereon, the force measurement system includes some type of force measurement device. Depending on the particular application, the force measurement device may take the form of a balance plate, force plate, jump plate, an instrumented treadmill, or some other device that is capable of quantifying the forces and moments exchanged between the body and the support surface.

Regardless of the type of force measurement device that is employed, the device is normally positioned on a support surface. In order for the device to be accurately considered as part of an inertial system, some type of rigid connection between the force measurement device and the ground on which it is placed must exist. However, in many applications, it is either impossible and/or undesirable to rigidly affix the force measurement device to the ground on which it is supported. For example, a force measurement plate used to conduct the dynamic testing of human subjects cannot be rigidly affixed to any support surface. Consequently, the force measurement assembly will move in space, and it will measure loads due to the inertia of the force measurement components in addition to the desired externally applied loads. For force measurement assemblies that have high masses, such as instrumented treadmills, these inertia forces will be comparable to, or even higher than the externally applied loads in magnitude. In such instances, it cannot be accurately assumed that the force measurement device is part of an inertial system, and it is necessary to compensate for the forces produced by the movement of the force measurement device, which results in undesirable measurement errors.

Motion acquisition/capture systems are used in numerous fields in order to record the motion of a moving body so that the movement and forces of the body can be analyzed. In a biomedical application, such as one involving gait analysis, a plurality of markers typically are provided on the body of a subject, and the movement of these markers is recorded in 3-dimensional space using a plurality of cameras positioned at various locations within a room. Then, once the positional data is obtained using the motion acquisition/capture system, inverse kinematics are employed in order to determine the joint angles of the subject. When the computation of the joint reaction forces and joint moments of the subject is also desired, the subject is often disposed on a force measurement device so that the ground reaction forces and moments associated with the subject can be measured. These ground reaction forces and moments are used in conjunction with the joint angles computed from the inverse kinematic analysis in order to determine the net joint reaction forces and net joint moments of the subject. In particular, inverse dynamics is used to calculate the net joint reaction forces and net joint moments of the subject by using the computed joint angles, angular velocities, and angular accelerations of a musculoskeletal model, together with the ground reaction forces and moments measured by the force measurement device.

However, the net joint reaction forces and net joint moments will not be accurately determined during the inverse dynamics analysis if the force measurement device, which is employed for measuring the ground reaction forces, is in motion. In such a case, the force measurement device will measure the loads due to the inertia of the force measurement components in addition to the desired ground reaction forces, which will introduce errors in the calculations. As described above, these errors will be quite substantial for force measurement assemblies having large masses, such as instrumented treadmills. Therefore, because the inertia of the force measurement assembly will result in substantial errors in the computed net joint reaction forces and net joint moments of the subject, compensation for the inertia of the force measurement system is necessary.

What is needed, therefore, is a force and/or motion measurement system having inertial compensation that accurately corrects for the movement of the force measurement device in multiple dimensions. Moreover, a force measurement and/or motion system is needed that is capable of empirically determining the inertial parameters of a large, complex force measurement assembly. While an analytical approach can be used for simple systems wherein the motion is limited to one direction, an analytical approach will not produce sufficiently accurate results for large systems that undergo complex multi-dimensional motion. Furthermore, a need exists for a force measurement system that produces accurate measurements when the entire system is in motion.

BRIEF SUMMARY OF THE INVENTION

Accordingly, the present invention is directed to a force and/or motion measurement system that substantially obviates one or more problems resulting from the limitations and deficiencies of the related art.

A first object of the present invention is to provide a force and/or motion measurement system with inertial compensation that is capable of accurately compensating for the non-inertial characteristics of a large measurement assembly which undergoes complex motions.

A second object of the present invention is to provide a force and/or motion measurement system with inertial compensation that employs a calibration procedure that is capable of accurately determining one or more inertial parameters of the system.

A third object of the present invention is to provide a force and/or motion measurement system with inertial compensation that is capable of accurately determining the location of the center of gravity of a complex measurement system.

A fourth object of the present invention is to provide a force and/or motion measurement system with inertial compensation that determines the inertial parameters of the force measurement system using applied motion profiles.

A fifth object of the present invention is to provide a force and/or motion measurement system with inertial compensation that produces accurate measurements when the force measurement assembly is in motion.

The aforedescribed objects are merely illustrative in nature, and in no way are intended to limit the scope of the claimed invention. Additional objects and advantages of the present invention will be apparent from the following detailed description, the accompanying drawings, and the appended claims.

To achieve one or more of these objects and advantages, in accordance with a first aspect of the present invention, there is provided a force measurement system having inertial compensation, which includes: a force measurement assembly configured to receive a subject, the force measurement assembly having a surface for receiving at least one portion of the body of the subject; at least one force transducer, the at least one force transducer configured to sense one or more measured quantities that are representative of forces and/or moments being applied to the surface of the force measurement assembly by the subject; a motion base operatively coupled to the force measurement assembly, the motion base configured to displace the force measurement assembly; an inertial compensation system operatively coupled to the force measurement assembly, the inertial compensation system configured to determine the inertial forces and/or moments resulting from the displacement of the force measurement assembly by the motion base; and a data manipulation means configured to convert the one or more measured quantities that are representative of the forces and/or moments being applied to the surface of the force measurement assembly by the subject into output forces and/or moments, the data manipulation means being further configured to correct the output forces and/or moments by utilizing the inertial forces and/or moments determined by the inertial compensation system such that the forces and/or moments being applied to the surface of the force measurement assembly are capable of being determined with a greater degree of accuracy.

In a preferred embodiment of this aspect of the present invention, the inertial compensation system is configured to determine both inertial forces and moments resulting from the displacement of the force measurement assembly.

In another preferred embodiment, the inertial compensation system utilizes a plurality of inertial parameters, which are determined for the force measurement assembly during a calibration procedure, for determining the inertial forces and moments resulting from the displacement of the force measurement assembly.

In yet another preferred embodiment, the inertial parameters include the mass of the force measurement assembly, the rotational inertia parameters of the force measurement assembly, and the position of the center of gravity of the force measurement assembly.

In still another preferred embodiment, the motion base is used for determining the plurality of inertial parameters of the force measurement assembly during the calibration procedure.

In yet another preferred embodiment, the motion base applies linear and/or rotational motion profiles to the force measurement assembly during the calibration procedure.

In yet another preferred embodiment, the force measurement assembly is in the form of a force plate or platform.

In still another preferred embodiment, the force measurement assembly is in the form of an instrumented treadmill.

In yet another preferred embodiment, a force plate is disposed underneath a treadmill belt.

In accordance with a second aspect of the present invention, there is provided a method for accurately determining the forces and/or moments applied to a surface of a force measurement device by a subject disposed thereon, which comprises the steps of: (a) providing a force measurement assembly configured to receive a subject thereon, the force measurement assembly having a surface for receiving at least one portion of the body of the subject and at least one force transducer, the at least one force transducer configured to sense one or more measured quantities that are representative of forces and/or moments being applied to the surface of the force measurement assembly by the subject; (b) providing a motion base operatively coupled to the force measurement assembly, the motion base configured to displace the force measurement assembly; (c) providing an inertial compensation system operatively coupled to the force measurement assembly, the inertial compensation system configured to determine the inertial forces and/or moments resulting from the displacement of the force measurement assembly; (d) positioning the subject on the force measurement assembly; displacing the force measurement assembly and the subject disposed thereon using the motion base; (e) determining, by using the inertial compensation system, the inertial forces and/or moments resulting from the displacement of the force measurement assembly by the motion base; (f) sensing, by utilizing the at least one force transducer, one or more measured quantities that are representative of forces and/or moments being applied to the surface of the force measurement assembly by the subject; (g) converting, by using a data manipulation device, the one or more measured quantities that are representative of the forces and/or moments being applied to the surface of the force measurement assembly by the subject into output forces and/or moments; and (h) correcting the output forces and/or moments by mathematically combining the output forces and/or moments with the inertial forces and/or moments determined by the inertial compensation system such that the forces and/or moments being applied to the surface of the force measurement assembly are determined with a greater degree of accuracy.

In a preferred embodiment of this aspect of the present invention, the method further includes the step of: determining, by using the inertial compensation system, both the inertial forces and moments resulting from the displacement of the force measurement assembly.

In another preferred embodiment, the method further includes the steps of: determining a plurality of inertial parameters for the force measurement assembly during a calibration procedure; and utilizing the plurality of inertial parameters in determining the inertial forces and moments resulting from the displacement of the force measurement assembly.

In yet another preferred embodiment, the inertial parameters include the mass of the force measurement assembly, the rotational inertia parameters of the force measurement assembly, and the position of the center of gravity of the force measurement assembly.

In yet another preferred embodiment, the method further includes the step of: using the motion base to determine the plurality of inertial parameters of the force measurement assembly during the calibration procedure.

In yet another preferred embodiment, the method further includes the step of: applying linear and/or rotational motion profiles to the force measurement assembly during the calibration procedure by using the motion base.

In accordance with a third aspect of the present invention, there is provided a force and/or motion measurement system with inertial compensation, which includes: a motion acquisition system having a plurality of motion sensing devices configured to capture the movement of a subject, the motion sensing devices generating a plurality of first measured quantities; a force measurement assembly configured to receive the subject, the force measurement assembly having a surface for receiving at least one portion of the body of the subject and at least one force transducer, the at least one force transducer configured to sense one or more second measured quantities that are representative of forces and/or moments being applied to the surface of the force measurement assembly by the subject; a motion base operatively coupled to the force measurement assembly, the motion base configured to displace the force measurement assembly; an inertial compensation system operatively coupled to the force measurement assembly, the inertial compensation system configured to determine the inertial forces and/or moments resulting from the displacement of the force measurement assembly by the motion base; and a data manipulation means being configured to convert the one or more second measured quantities that are representative of the forces and/or moments being applied to the surface of the force measurement assembly by the subject into output forces and/or moments, the data manipulation means being further configured to correct the output forces and/or moments by utilizing the inertial forces and/or moments determined by the inertial compensation system, and the data manipulation means being additionally configured to determine forces and/or moments at one or more joints of the subject by using the corrected output forces and/or moments in combination with force and/or moment data generated from the plurality of first measured quantities.

In a preferred embodiment of this aspect of the present invention, the inertial compensation system is configured to determine both inertial forces and moments resulting from the displacement of the force measurement assembly.

In another preferred embodiment, the inertial compensation system utilizes a plurality of inertial parameters, which are determined for the force measurement assembly during a calibration procedure, for determining the inertial forces and moments resulting from the displacement of the force measurement assembly.

In yet another preferred embodiment, the inertial parameters include the mass of the force measurement assembly, the rotational inertia parameters of the force measurement assembly, and the position of the center of gravity of the force measurement assembly.

In still another preferred embodiment, the motion base is used for determining the plurality of inertial parameters of the force measurement assembly during a calibration procedure.

In yet another preferred embodiment, the motion base applies linear and/or rotational motion profiles to the force measurement assembly during the calibration procedure.

In still another preferred embodiment, the force measurement assembly is in the form of a force plate or platform.

In yet another preferred embodiment, the force measurement assembly is in the form of an instrumented treadmill.

In still another preferred embodiment, a force plate is disposed underneath a treadmill belt.

It is to be understood that the foregoing objects and summary, and the following detailed description of the present invention, are merely exemplary and explanatory in nature. As such, the foregoing objects and summary, and the following detailed description of the invention, should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 4a is a schematic side view of a force measurement assembly with the location of an accelerometer and an angular velocity sensor depicted thereon according to an embodiment of the invention;

FIG. 4b is a schematic front view of a force measurement assembly with the location of an accelerometer and an angular velocity sensor depicted thereon according to an embodiment of the invention;

FIG. 5a is a schematic side view of a force measurement assembly with the location of a plurality of accelerometers and a plurality of angular velocity sensors depicted thereon according to an embodiment of the invention;

FIG. 5b is a schematic front view of a force measurement assembly with the location of a plurality of accelerometers and a plurality of angular velocity sensors depicted thereon according to an embodiment of the invention;

FIG. 7a is a schematic side view of a force transducer with the location of a plurality of accelerometers and a plurality of angular velocity sensors depicted thereon according to an embodiment of the invention;

FIG. 7b is a schematic front view of a force transducer with the location of a plurality of accelerometers and a plurality of angular velocity sensors depicted thereon according to an embodiment of the invention;

Throughout the figures, the same parts are always denoted using the same reference characters so that, as a general rule, they will only be described once.

DETAILED DESCRIPTION OF THE INVENTION

Figure 1:
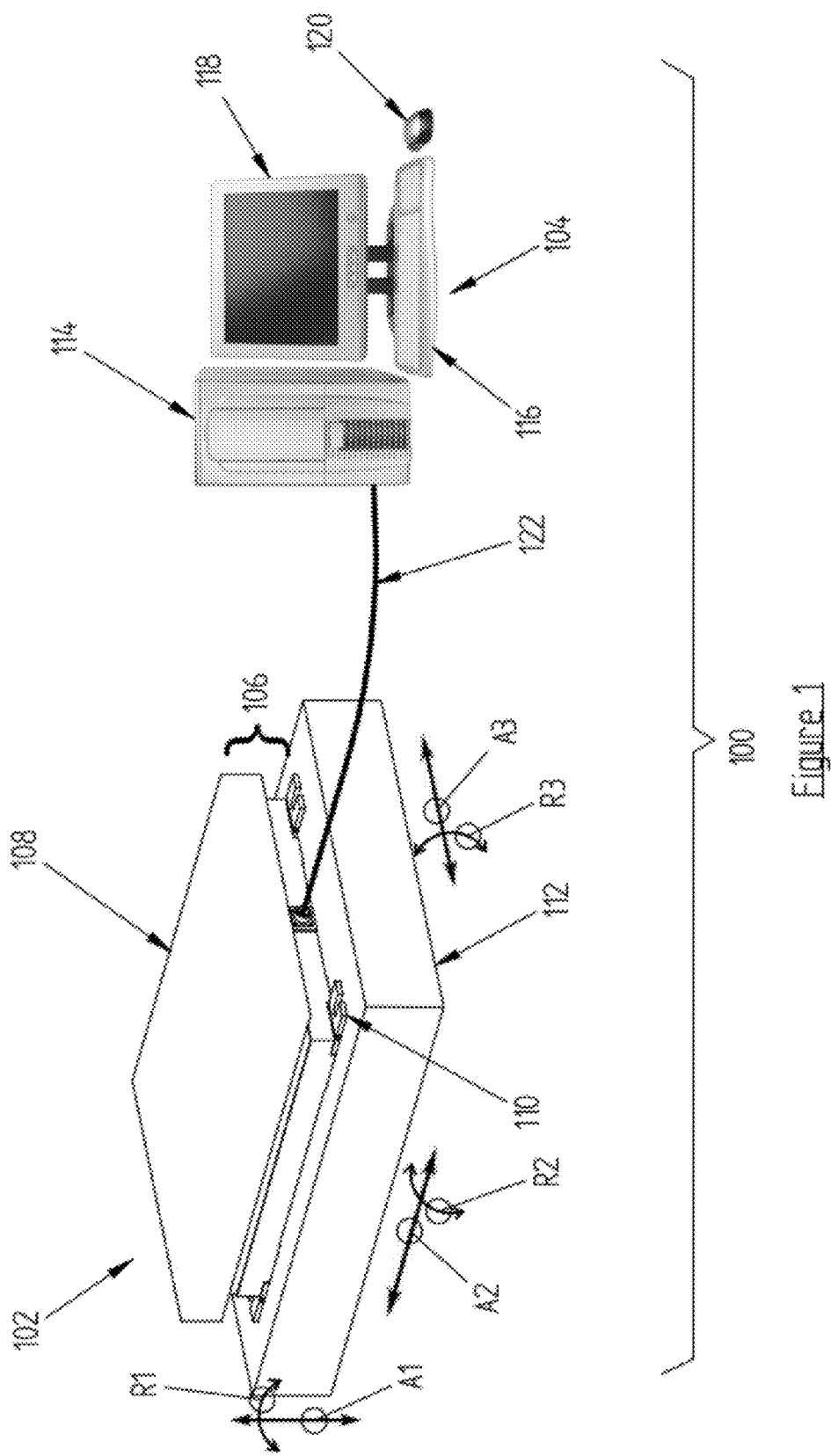
FIG. 1 is a diagrammatic perspective view of a force measurement system according to a first embodiment of the invention, wherein the force measurement assembly is in the form of a force plate or platform.

A first embodiment of the force measurement system is seen generally at 100 in FIG. 1. The force measurement system 100 generally comprises a force measurement assembly 102 operatively coupled to a data acquisition/data processing device 104 by virtue of an electrical cable 122. In the first embodiment, the force measurement assembly 102 for receiving a subject is in the form of a force plate or platform. In a preferred embodiment of the invention, the electrical cable 122 is used for data transmission, as well as for providing power to the force measurement assembly 102. Preferably, the electrical cable 122 contains a plurality of electrical wires bundled together, with at least one wire being used for power and at least another wire being used for transmitting data. The bundling of the power and data transmission wires into a single electrical cable 122 advantageously creates a simpler and more efficient design. In addition, it enhances the safety of the testing environment when human subjects are being tested on the force measurement assembly 102. However, it is to be understood that the force measurement assembly 102 can be operatively coupled to the data acquisition/data processing device 104 using other signal transmission means, such as a wireless data transmission system. If a wireless data transmission system is employed, it is preferable to provide the force measurement assembly 102 with a separate power supply in the form of an internal power supply or a dedicated external power supply.

Referring again to FIG. 1, it can be seen that the force measurement assembly 102 according to the first embodiment of the invention, includes a force plate or platform 106 that is attached to the top of a motion base 112 via a plurality of mounting brackets 110. The force plate or platform 106 has a top surface 108 that is configured to receive at least one portion of a body of a subject. In a preferred embodiment, a subject stands in an upright position atop the force plate 106 and the feet of the subject are placed on its top surface 108. In FIG. 1, the arrows A1, A2, A3 disposed adjacent to the motion base 112 schematically depict the displaceable nature of the force measurement assembly 102, which is effectuated by the motion base 112. Moreover, the curved arrows R1, R2, R3 in FIG. 1 schematically illustrate the ability of the force measurement assembly 102 to be rotated about a plurality of different axes, the rotational movement of the force measurement assembly 102 is also generated by the motion base 112.

As shown in FIG. 1, the data acquisition/data processing device 104 generally includes a central processing unit (CPU) 114 for collecting and processing the data that is received from the force measurement assembly 102, which has a plurality of peripheral devices 116-120 connected thereto. Preferably, the peripheral devices that are operatively coupled to the central processing unit 114 comprise user input devices 116, 120 in the form of a keyboard 116 and a mouse 120, as well as a graphical user interface in the form of a monitor 118. While a desktop type computing system is depicted in FIG. 1, one of ordinary of skill in the art will appreciate that another type of data acquisition/data processing device 104 can be substituted for the desktop computing system such as, but not limited to, a laptop or a palmtop computing device (i.e., a PDA). In addition, rather than providing a data acquisition/data processing device 104, it is to be understood that only a data acquisition device could be provided without departing from the spirit and the scope of the claimed invention.

Figure 2:
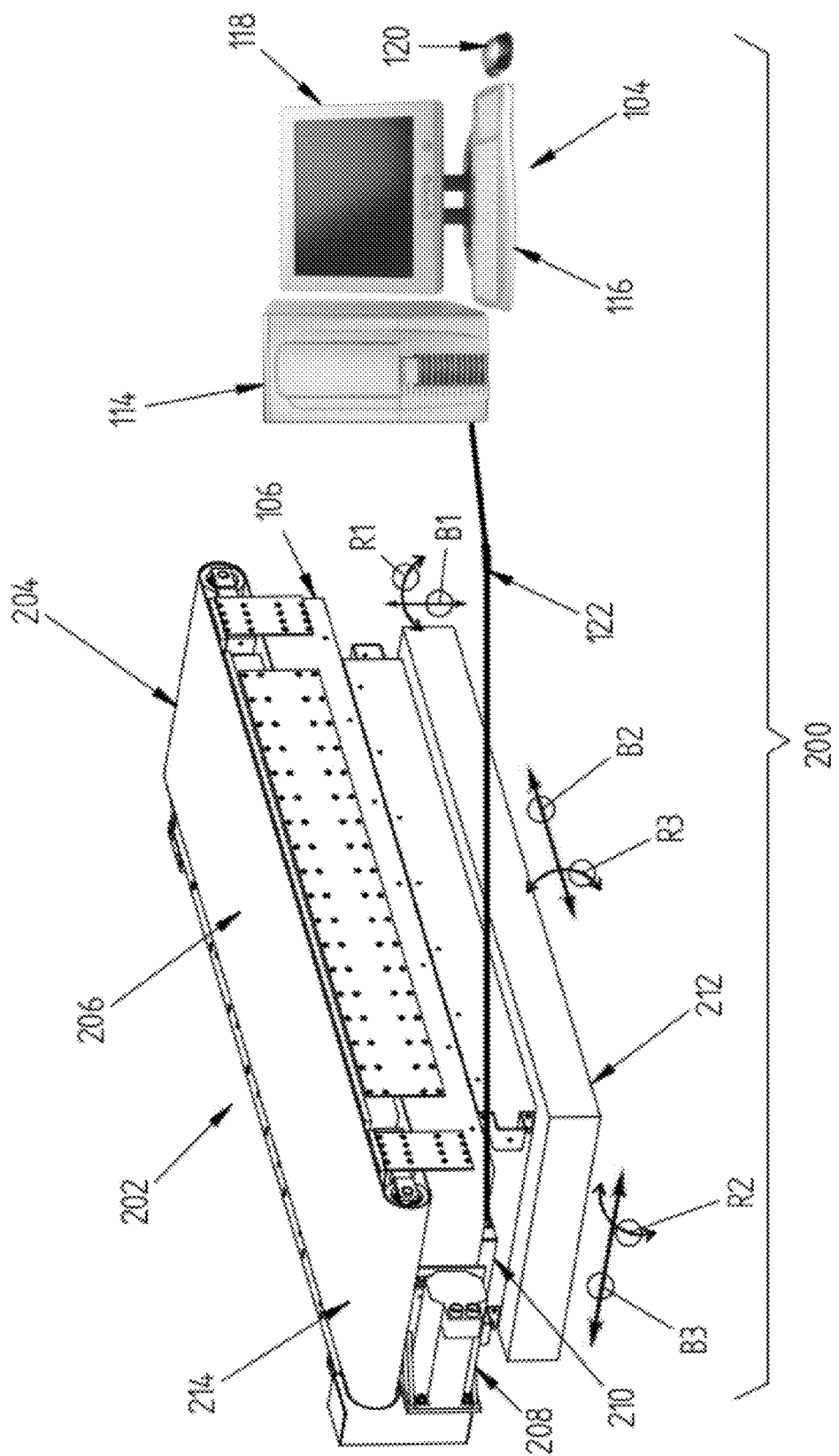
FIG. 2 is a diagrammatic perspective view of a force measurement system according to a second embodiment of the invention, wherein the force measurement assembly is in the form of an instrumented treadmill.

A second embodiment of the force measurement system is seen generally at 200 in FIG. 2. In accordance with the second embodiment of the invention, the force measurement system 200 generally comprises a force measurement assembly 202 operatively coupled to a data acquisition/data processing device 104 by virtue of an electrical cable 122. In the second embodiment, the force measurement assembly 202 for receiving a subject is in the form of an instrumented treadmill. Because the data acquisition/data processing device 104 and the electrical cable 122 are the same as that described above with regard to the first embodiment, a description of these components 104, 122 will not be repeated for this embodiment.

As illustrated in FIG. 2, the force measurement assembly 202 according to the second embodiment of the invention includes a treadmill 204 that is attached to the top of a motion base 212. The treadmill 204 has a top surface 206 that is configured to receive at least one portion of a body of a subject. In a preferred embodiment, a subject walks or runs in an upright position atop the treadmill 204 with the feet of the subject contacting the top surface 206 of the treadmill 204. The belt 214 of the treadmill 204 is rotated by an electric actuator assembly 208, which generally comprises an electric motor. The electrical cable 122 is operatively coupled to a load output device 210, which is at one end of the treadmill 204, and beneath the rotating belt 214. While it is not readily visible in FIG. 2 due to its location, the force measurement assembly 202, like the force measurement assembly 102, includes a force plate 106 with a plurality of force transducers disposed below the rotating belt 214 of the treadmill 204 so that the load being applied to the top surface 206 can be measured. Also, similar to FIG. 1, the arrows B1, B2, B3 disposed adjacent to the motion base 212 in FIG. 2 schematically depict the displaceable nature of the force measurement assembly 202, which is effectuated by the motion base 212. Moreover, as in FIG. 1, the curved arrows R1, R2, R3 in FIG. 2 schematically illustrate the ability of the force measurement assembly 202 to be rotated about a plurality of different axes, the rotational movement of the force measurement assembly 202 being generated by the motion base 212.

While the exemplary force measurement systems 100, 200 explained above employ force measurement assemblies 102, 202 that are configured to receive a subject in an upright position, it is to be understood that the invention is not so limited. Rather, the present invention can be practiced with a force measurement assembly that accommodates a subject in a position other than an upright position, such as a supine position. One such example of a force measurement assembly that receives a subject in a supine position is a ballistocardiographic bed.

Figure 3B:
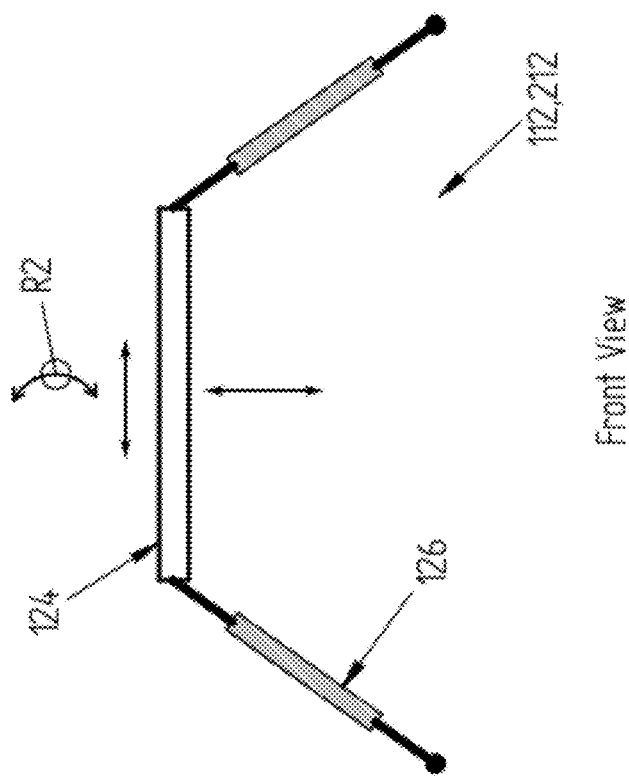
FIG. 3b is a schematic front view of a motion base according to an embodiment of the invention.
Figure 3A:
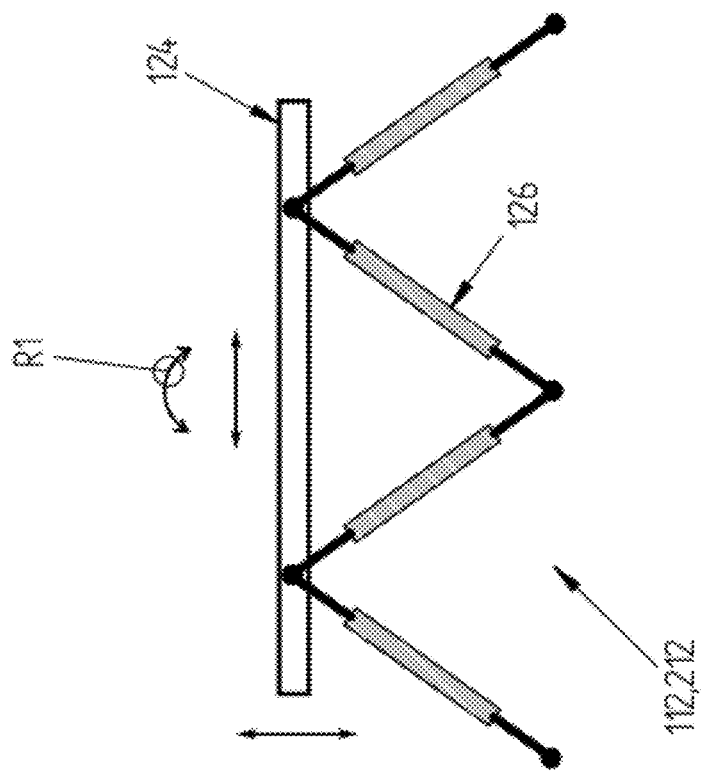
FIG. 3a is a schematic side view of a motion base according to an embodiment of the invention.

The primary components of the motion base 112, 212 are schematically depicted in FIGS. 3a and 3b. As depicted in these figures, the motion base 112, 212 comprises a movable top surface 124 that is preferably displaceable (represented by straight arrows) and rotatable (illustrated by curved arrows R1, R2) in 3-dimensional space by means of a plurality of actuators 126. In both the first and second embodiments, the force plate 106 is disposed on the movable top surface 124. The motion base 112, 212 performs several functions in the force measurement system. First, the motion base 112, 212 is used for the dynamic testing of subjects when, for example, the subject is being tested in a virtual reality environment. Secondly, the motion base 112, 212 is used during the calibration procedure of the force measurement systems 100, 200 in order to generate applied linear and/or rotational motion profiles that are applied to the force measurement assemblies 102, 202 so that the inertial parameters of the force measurement assembly 102, 202 can be determined. While the motion base 112, 212 is preferably displaceable and rotatable in 3-dimensional space, it is to be understood that the present invention is not so limited. Rather, motion bases 112, 212 that only are capable of 1 or 2 dimensional motion could be provided without departing from the spirit and the scope of the claimed invention. Also, motion bases 112, 212 that are only capable of either linear motion or rotational motion are encompassed by the present invention.

In FIGS. 4a and 4b, an accelerometer 128 and an angular velocity sensor 130 are schematically depicted on a force measurement assembly 102. While the exemplary force measurement assembly 102 depicted in FIGS. 4a and 4b more closely resembles that of the first embodiment, it is to be understood that FIGS. 4a and 4b are equally applicable to the second embodiment of the invention, wherein the force measurement assembly 202 includes a treadmill 204. As described above, the force plate 106 is disposed below the rotating belt 214 of the treadmill 204 so that the load being applied by the subject disposed on the top surface 206 can be determined. As shown in FIGS. 4a and 4b, the force plate 106 comprises a top plate assembly 132 with a top surface 108 supported on a plurality of force transducers 134. While a total of four (4) force transducers 134 are depicted in FIGS. 4a and 4b (i.e., one force transducer 134 being located near each corner of the top plate assembly 132, one of ordinary skill in the art will appreciate that a different quantity of force transducers may be used (i.e., more than four or less than four) without departing from the spirit and scope of the claimed invention. In these figures, an accelerometer 128 and an angular velocity sensor 130 are shown spaced apart internally within the top plate assembly 132. Although, it is to be understood that the placement of the accelerometer 128 and the angular velocity sensor 130 is not limited to any particular location on the top plate assembly 132 of the force plate 106. Rather, the accelerometer 128 and the angular velocity sensor 130 can be placed virtually anywhere on the force plate 106.

FIGS. 5a and 5b are similar in most respects to FIGS. 4a and 4b described above, except that a plurality of accelerometers 128 are depicted, rather than a single accelerometer 128, as well as a plurality of angular velocity sensors 130. In particular, the exemplary embodiment of FIGS. 5a and 5b depicts three accelerometers 128 being provided with two angular velocity sensors 130. However, as described above with regard to FIGS. 4a and 4b, the invention is in no way limited to the specific quantity of devices 128, 130 depicted in FIGS. 5a and 5b. Rather, one of ordinary skill in the art will appreciate that varying the quantities of accelerometers 128 and angular velocity sensors 130 are encompassed by the claimed invention. Moreover, as explained above with respect to FIGS. 4a and 4b, the placement of each accelerometer 128 and angular velocity sensor 130 is not limited to any particular location within the top plate assembly 132 of the force plate 106, rather the location of the devices 128, 130 can be varied.

Figure 6B:
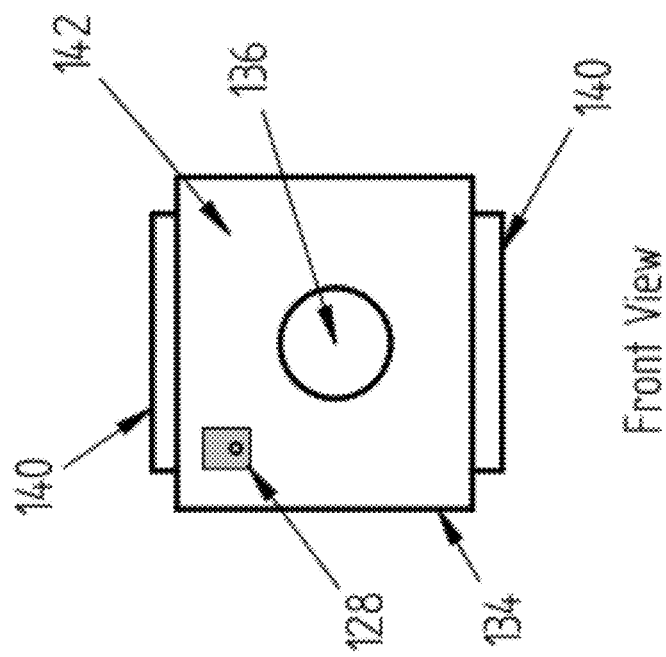
FIG. 6b is a schematic front view of a force transducer with the location of an accelerometer depicted thereon according to an embodiment of the invention.
Figure 6A:
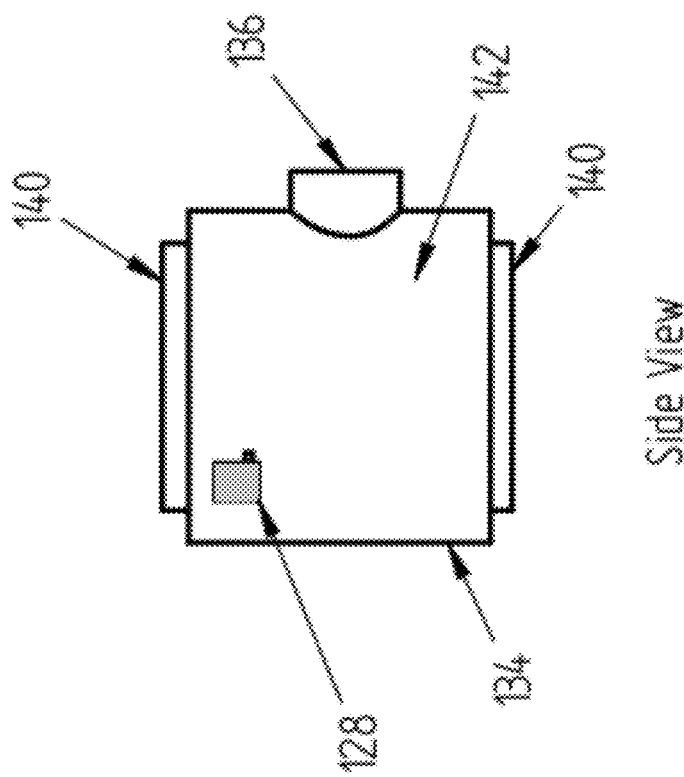
FIG. 6a is a schematic side view of a force transducer with the location of an accelerometer depicted thereon according to an embodiment of the invention.

FIGS. 6a and 6b schematically represent a force transducer 134 having an accelerometer 128 disposed thereon. While the force transducer 134 depicted in FIGS. 6a and 6b is a pylon-type transducer, which has a generally cylindrical shape, one of ordinary skill in the art will appreciate that the present invention can be practiced with other types of force transducers such as, but not limited to, beam-type force transducers. In the exemplary embodiments depicted in FIGS. 4a-4b and 5a-5b, each force transducer 134 is disposed between the bottom surface of the top plate assembly 132 and the top surface of the motion base 112. As shown in FIGS. 6a and 6b, the force transducer 134 has a force transducer sensing element 140 disposed within a cylindrical casing 142. In a preferred embodiment of the invention, the force transducer sensing element 140 includes a plurality of strain gages wired in a Wheatstone bridge configuration, wherein the electrical resistance of each strain gage is altered when the force transducer sensing element 140 undergoes deformation resulting from the forces and/or moments acting on the force plate 106. Thus, the force transducer sensing element 140 senses mechanical strains that are representative of the forces and/or moments being applied to the force plate 106. Also, as depicted in these figures, an electrical connector 136 is disposed on one side of the cylindrical casing 142. The electrical connector 136 is operatively connected to one or more wires that transmit the output signal(s) of the force transducer sensing element 140 to a signal amplifier/converter and/or data acquisition/data processing device 104. Moreover, as described above for accelerometer(s) being mounted on the top plate assembly 132, the quantity of accelerometers 128, and the location of each accelerometer 128, can be varied from that which is depicted in the exemplary embodiment of FIGS. 6a and 6b. Also, although not explicitly shown, the force transducer 134 can be provided with one or more angular velocity sensors 130 disposed thereon or therein.

FIGS. 7a and 7b are similar to FIGS. 6a and 6b described above, except that a plurality of accelerometers 128 are depicted, rather than a single accelerometer 128. Also, a plurality of angular velocity sensors 130 are shown on the force transducer 134. In particular, the exemplary embodiment of FIGS. 7a and 7b depicts three accelerometers 128 being provided with two angular velocity sensors 130. However, as described above with regard to FIGS. 5a-5b and 6a-6b, the invention is in no way limited to the specific quantity of devices 128, 130 depicted in FIGS. 7a and 7b. Rather, one of ordinary skill in the art will appreciate that varying quantities of accelerometers 128 and angular velocity sensors 130 are encompassed by the claimed invention. Moreover, the placement of each accelerometer 128 and each angular velocity sensor 130 is not limited to any particular location on the force transducer 134, rather the location of the devices 128, 130 can be varied.

Figure 8:
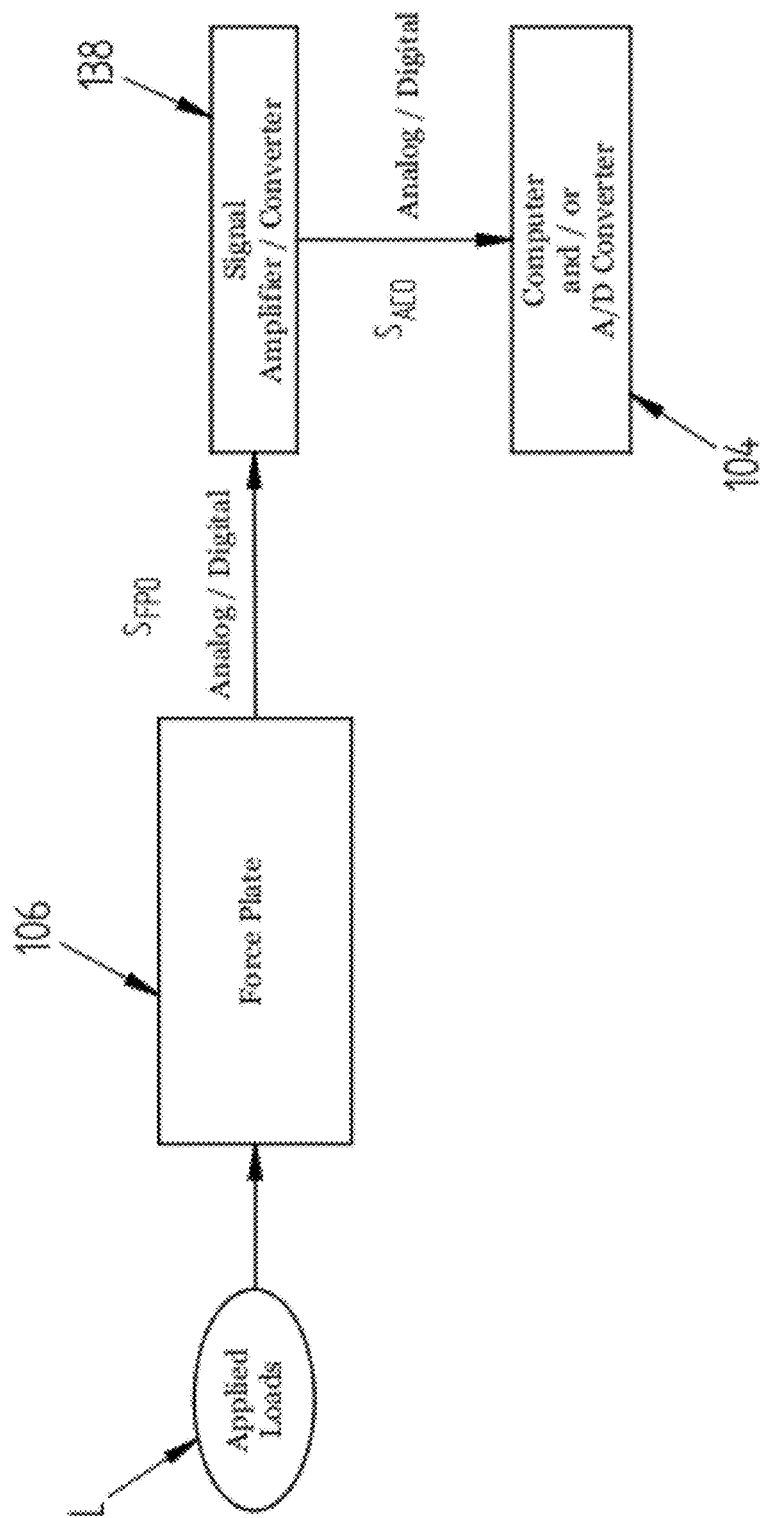
FIG. 8 is a block diagram illustrating the data acquisition/data processing system according to an embodiment of the invention.

FIG. 8 graphically illustrates the acquisition and processing of the load data carried out by the force measurement systems 100, 200. Initially, as shown in FIG. 8, a load L is applied to the force plate 106 by a subject disposed thereon. After which, the force plate 106 transmits a force plate output signal(s) $S_{FPO}$ to a signal amplifier/converter 138. Depending on the hardware that is employed, the force plate output signal(s) $S_{FPO}$ can be either in the form of an analog signal(s) or a digital signal(s). The signal amplifier/converter 138 magnifies the force plate output signal(s) $S_{FPO}$, and if the signal(s) $S_{FPO}$ is of the analog-type, it may also convert the analog signal(s) to a digital signal(s). Then, the signal amplifier/ converter 138 transmits either a digital or analog signal(s) $S_{ACO}$ to a data acquisition/data processing device 104 so that the forces and moments that are being applied to the surface of the force measurement assembly 102, 202 can be outputted to a user. In addition to a computer, which generally includes a central processing unit (CPU) 114, graphical user interface 118, and a plurality of user input devices 116, 120, the data acquisition/data processing device 104 may further comprise an analog-to-digital (A/D) converter if the signal(s) $S_{ACO}$ is in the form of an analog signal(s). In such a case, the analog-to-digital converter will convert the analog signal(s) into a digital signal(s) for processing by a central processing unit 114. In one exemplary embodiment of the invention, the signal amplifier/converter 138 and the central processing unit (CPU) 114 of the data acquisition/data processing device 104 form a data manipulation means, which is configured to convert one or more measured quantities (e.g., mechanical strains) that are representative of the forces and/or moments being applied to the surface of the force measurement assembly by the subject into output forces and/or moments.

In a preferred embodiment of the invention, the output forces and moments of the data acquisition/data processing device 104 comprise the three (3) orthogonal components of the resultant force acting on the force plate 106 and the three (3) orthogonal components of the resultant moment acting on the force plate 106, respectively. However, it is to be understood that, in other embodiments of the invention, the output forces and moments of the data acquisition/data processing device 104 can be in the form of other forces and moments as well.

Now, the inertial compensation system of the present invention will be described in detail. In a preferred embodiment of the invention, the inertial compensation system generally includes, but is not limited to, the following hardware components: at least one acceleration sensor 128, at least one angular velocity sensor 130, and a data acquisition/data processing device 104. Also, in a preferred embodiment, the inertial compensation system of the present invention advantageously employs a calibration procedure that empirically determines the inertial parameters of the force measurement assembly 102, 202 using applied linear and/or rotational motion profiles executed by the motion base 112, 212 of the force measurement system 100, 200. In particular, the motion base 112, 212 is programmed in order to displace the force measurement assembly using a set of applied motion profiles. The calibration procedure described hereinafter is particularly well suited to large force measurement assemblies that undergo complex motions such as, but not limited to, instrumented treadmill systems. The procedure also produces accurate results for force measurement systems wherein the entire system is moving. There are no assumptions made about the system, rather the procedure utilizes three-dimensional (3-D) equations of motion such that every inertial parameter is identified by the calibration procedure. In a preferred embodiment of the invention, the calibration procedure is embodied in a computer-readable medium loaded on the data acquisition/data processing device 104.

Figure 9:
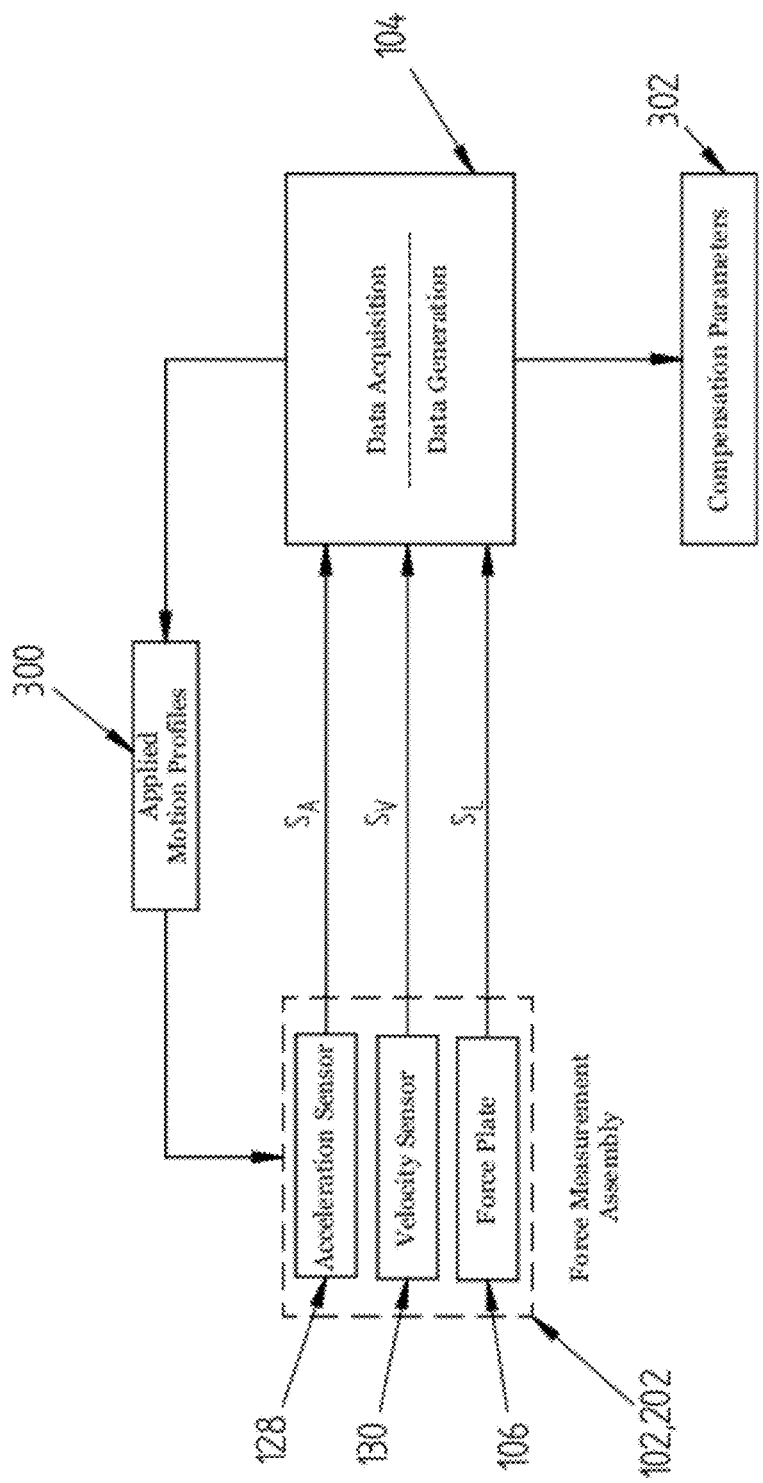
FIG. 9 is a block diagram illustrating a calibration routine of the force measurement system according to an embodiment of the invention.

In FIG. 9, a preferred embodiment of the calibration procedure of the force measurement systems 100, 200 is graphically depicted. Initially, the central processing device 114 of the data acquisition/data processing device 104 executes a calibration procedure stored on a computer-readable medium. At the beginning of the calibration procedure, a plurality of applied motion profiles 300 are applied to the force measurement assembly 102, 202. While the force measurement assembly 102, 202 is being subjected to the applied motion profiles 300, signals $S_A$, $S_V$, and $S_L$ from the acceleration sensor 128, angular velocity sensor 130, and force plate 106, respectively, are transmitted to the data acquisition/data processing device 104 so that these signals $S_A$, $S_V$, and $S_L$ can undergo processing. Signals $S_A$, $S_V$, and $S_L$ are collected while the force measurement assembly 102, 202 is subjected to a plurality of different, applied motion profiles. After each applied motion profile 300 is executed, the values of the compensation parameters 302 are determined.

In a preferred embodiment, the applied motion profiles 300 are sinusoidal and/or sawtooth waveforms generated by the motion base 112, 212. A variety of different motion profiles can be utilized for effectively calibrating the force measurement systems 100, 200. However, if the motion base 112, 212 is used to generate the motion profiles 300, the amplitudes and the frequencies of the waveforms that are used for the calibration procedure are limited to that which is capable of being produced by the motion base 112, 212. Although, it is to be understood that, as an alternative to using the motion base 112, 212, the applied motion profiles 300 may be applied to the force measurement assembly 102, 202 by utilizing another device or by the manual application thereof.

In order to better illustrate the calibration procedure summarized above, the mathematical calculations carried out by the data acquisition/data processing device 104 will be explained. The equations that describe the force inertia relationship for the moving force measurement assemblies 102, 202 are as follows:

$$m \cdot \vec{a}_G = \vec{F}_m + \vec{F}_e \quad (1)$$

$$\vec{J}\dot{\vec{\omega}} + \vec{\omega} \times \vec{J}\vec{\omega} = \vec{M}_m + \vec{M}_e + \vec{r}_G \times (\vec{F}_m + \vec{F}_e) \quad (2)$$

where:
m: mass of the system inertia measured by the transducer
$\vec{a}_G$: acceleration of mass m
$\vec{F}_m$: measured forces from the transducer(s)
$\vec{F}_e$: externally applied forces
$J$: rotational inertia of the system
$\dot{\vec{\omega}}$: angular acceleration of the system
$\vec{\omega}$: angular velocity of the system
$\vec{M}_m$: measured moments from the transducer(s)
$\vec{M}_e$: externally applied moments
$\vec{r}_G$: position vector of the center of gravity.

As equations (1) and (2) clearly illustrate, the measured forces $\vec{F}_m$ and moments $\vec{M}_m$ are mathematically distinct from the externally applied forces $\vec{F}_e$ and moments $\vec{M}_e$. The load output (i.e., forces $\vec{F}_m$ and moments $\vec{M}_m$) of the force measurement assembly 102, 202 is measured using the force transducers 134 with force transducer elements 140 disposed thereon. The term $m \cdot \vec{a}_G$ on the left side of equation (1) denotes the inertial "forces", whereas the term $\vec{J}\dot{\vec{\omega}} + \vec{\omega} \times \vec{J}\vec{\omega}$ on the left side of equation (2) denotes the inertial "moments". In a preferred embodiment of the invention, compensating for the inertia loads of the force measurement assembly 102, 202 requires independent measurement of the accelerations and angular velocities experienced thereby. These measurements are capable of being performed using commercially available accelerometers and angular velocity sensors (rate gyroscopes). In the preferred embodiment, three 3-component linear accelerometers and a 3-component angular velocity sensor (rate gyroscope) are used to measure the kinematics (e.g., parameters $\vec{a}_G$ and $\vec{\omega}$) of the force measurement assembly 102, 202. The equations that describe the kinematics of the force measurement assembly 102, 202 using the accelerometers at three (3) non-collinear points $P_1$, $P_2$, $P_3$ and center of mass G are as follows:

$$\vec{a}_{P1} = \vec{a}_{P2} + \vec{\omega} \times \vec{r}_{12} + \vec{\omega} \times (\vec{\omega} \times \vec{r}_{12}) \quad (3)$$

$$\vec{a}_{P2} = \vec{a}_{P3} + \vec{\omega} \times \vec{r}_{23} + \vec{\omega} \times (\vec{\omega} \times \vec{r}_{23}) \quad (4)$$

$$\vec{a}_G = \vec{a}_{P1} + \vec{\omega} \times \vec{r}_{G1} + \vec{\omega} \times (\vec{\omega} \times \vec{r}_{G1}) \quad (5)$$

where:

$\vec{a}_{P1}, \vec{a}_{P2}, \vec{a}_{P3}$: measured accelerations at points $P_1$, $P_2$ and $P_3$ respectively $\vec{r}_{12}, \vec{r}_{23}$: position vectors from $P_2$ to $P_1$ and $P_3$ to $P_2$ respectively $\vec{r}_{G1}$: position vector from point $P_1$ to mass center G.

In equations (3)-(5) above, the position vectors $\vec{r}_{12}, \vec{r}_{23}$ are preferably determined prior to the commencement of the calibration procedure using an analytical method. For example, the position vectors $\vec{r}_{12}, \vec{r}_{23}$ can be determined from computerized drawings of the force measurement assembly 102, 202 by utilizing a computer-assisted design (CAD) program. Although, one of ordinary skill in the art will appreciate that the position vectors $\vec{r}_{12}, \vec{r}_{23}$ can also be determined using other methods without departing from the spirit and the scope of the invention.

Measurement system constants (compensation parameters 302), such as mass m, rotational inertia $\bar{J}$, and geometric parameters of the system are needed in order to solve equations (1) and (2) above. These parameters are determined by subjecting the force measurement assembly 102, 202 to a plurality of applied motion profiles 300 such that, after each motion profile is executed, the values of the system constants are determined. In a preferred embodiment, an unloaded force measurement assembly 102, 202 initially is displaced using a linear acceleration profile in order to simplify the mathematical determination of the mass m. Because both $\vec{F}_e = 0$ and $\vec{M}_e = 0$ for the unloaded force measurement assembly 102, 202, the mass m can be determined using equation (1). Moreover, because the angular velocity $\vec{\omega}$ and the angular acceleration $\dot{\vec{\omega}}$ are both equal to zero when the unloaded force measurement assembly 102, 202 is subjected to only a linear acceleration, the position vector of the center of gravity $\vec{r}_G$ can be computed from equation (2), wherein the term $\bar{J}\dot{\vec{\omega}} + \vec{\omega} \times \bar{J}\vec{\omega}$ is equal to zero and drops out of equation (2). Then, different motion profiles involving angular accelerations and angular velocities are applied to the force measurement assembly 102, 202 so that the angular acceleration $\dot{\vec{\omega}}$ can be solved from the over-determined set of equations (3) and (4) by using the accelerations measured by the three accelerometers and the angular velocity $\vec{\omega}$ measured by the angular velocity sensor (rate gyroscope). Finally, the elements of the rotational inertia matrix $\bar{J}$ can be solved using equation (2). By following the aforementioned procedural steps, all of the inertial and geometric constants of the force measurement assembly 102, 202 can be determined.

While a linear acceleration profile is used for the displacement of the unloaded force measurement assembly 102, 202 in the preferred embodiment so as to facilitate the computational determination of the mass m, it is to be understood that the present invention is not so limited. Rather, a non-linear acceleration profile can be applied to the unloaded force measurement assembly 102, 202. In such a case, rather than simply using equation (1), the mass m will be determined along with the other measurement system constants by simultaneously solving equations (1) and (2) and using the mathematical relationships set forth in equations (3)-(5).

Figure 10:
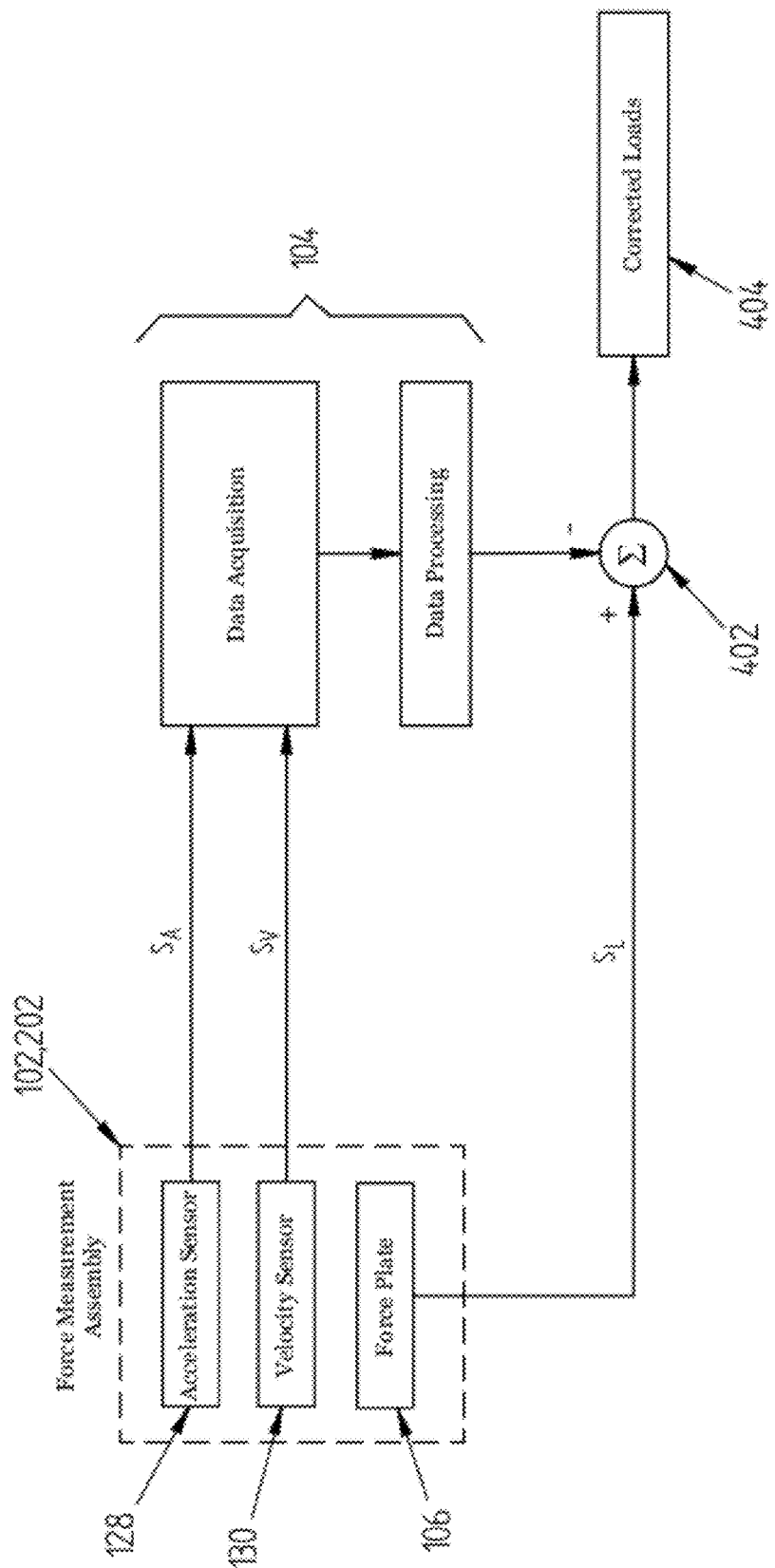
FIG. 10 is a block diagram illustrating a compensation procedure of the force measurement system according to an embodiment of the invention.

A preferred embodiment of the inertial compensation procedure of the force measurement systems 100, 200 is graphically depicted in FIG. 10. After the calibration procedure described above has been performed, the signals $S_A$ and $S_V$ from the acceleration sensor 128 and angular velocity sensor 130, respectively, are fed into the data acquisition/data processing device 104 and mathematically combined with the values of the compensation parameters determined during the calibration procedure. Then, the load signals $S_L$ from the force transducers of the force plate 106 are mathematically combined with the computed forces and moments due to the inertia of the system at 402 (preferably using the data acquisition/data processing device 104 to perform these mathematical computations). Once the load signals $S_L$ have been combined with the computed inertia forces and moments, a corrected load output 404 is obtained.

Now, to further explain the inertial compensation procedure summarized above, the mathematical manipulations carried out by the data acquisition/data processing device 104 will be explained. During the inertial calibration procedure, the mass m, the rotational inertia $\bar{J}$, and at least one geometric parameter (e.g., the position of the center of mass $\vec{r}_G$) of the force measurement assembly 102, 202 were determined. These inertial parameters (m, $\bar{J}$, and the at least one geometric parameter) are used in conjunction with the signals $S_A$ and $S_V$ from the acceleration sensor(s) 128 and the angular velocity sensor 130, and load signals $S_L$ from the force transducers 134, of the force plate 106 in order to compute the desired externally applied forces $\vec{F}_e$ and moments $\vec{M}_e$ using the following two equations:

$$\vec{F}_e = m \cdot \vec{a}_G - \vec{F}_m \quad (6)$$

$$\vec{M}_e = \bar{J}\dot{\vec{\omega}} + \vec{\omega} \times \bar{J}\vec{\omega} - \vec{M}_m - \vec{r}_G \times (\vec{F}_m + \vec{F}_e) \quad (7)$$

Equations (6) and (7) are similar to equations (1) and (2) discussed above, except that the terms in these two equations have been rearranged in order to solve for the desired externally applied forces $\vec{F}_e$ and moments $\vec{M}_e$. Inertia compensation of the load measurement requires using the measured values for $\vec{\omega}$, and $\dot{\vec{\omega}}$ together with equations (3), (4), and (5), and the load output of the force transducers 134, such that the externally applied forces $\vec{F}_e$ and moments $\vec{M}_e$ can be computed using equations (6) and (7). Because all of the fixed system parameters, such as the mass m and the rotational inertia matrix $\bar{J}$, are computed in the inertial calibration stage, the unknown externally applied loads $\vec{F}_e$ and $\vec{M}_e$ can be solved using equations (6) and (7). Thus, after the above described mathematical manipulations have been performed, the unwanted inertial effect of the force measurement assembly 102, 202 has been eliminated from the output load determined by the force measurement systems 100, 200.

Figure 11:
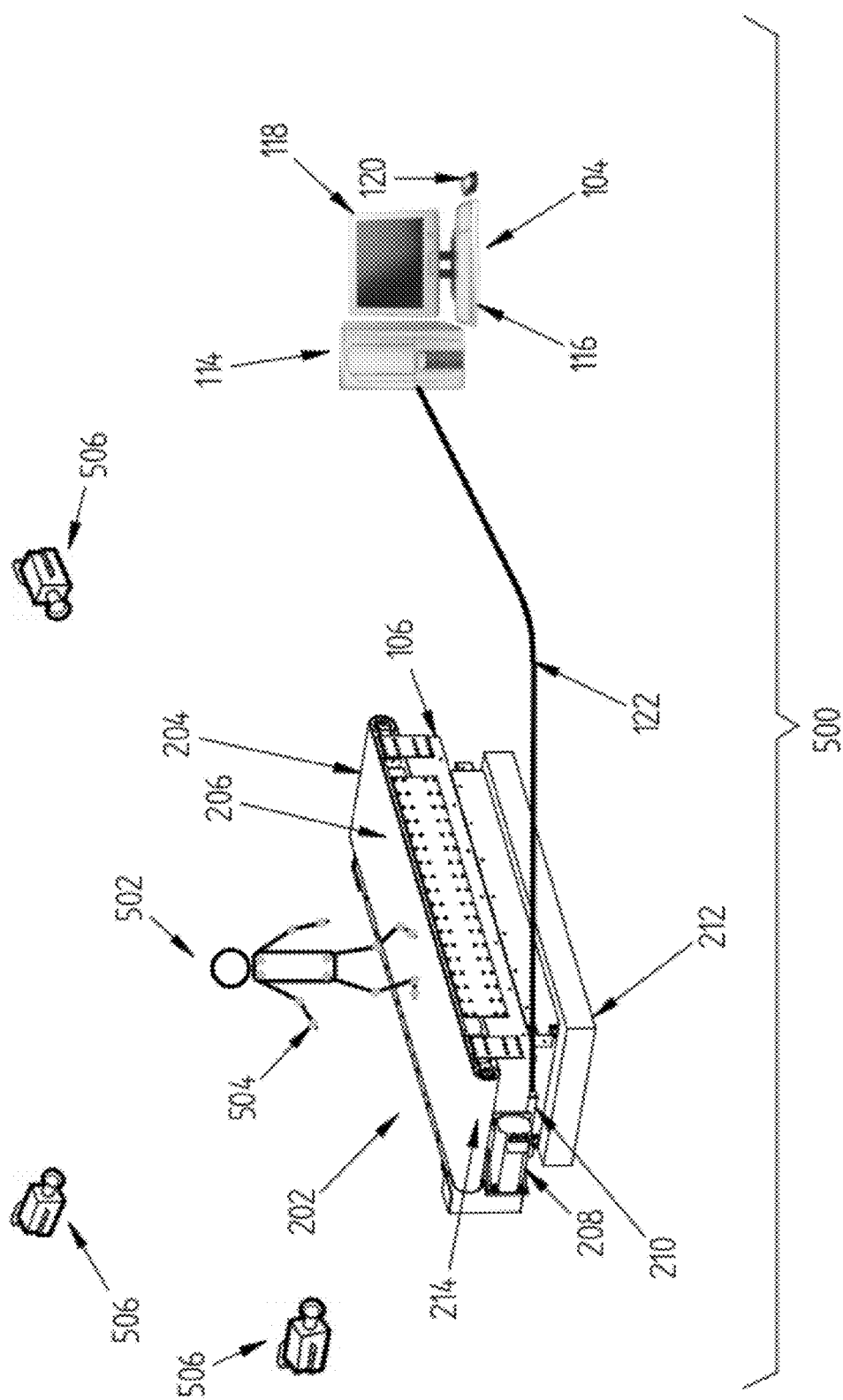
FIG. 11 is a diagrammatic perspective view of a force and motion measurement system according to an embodiment of the invention, wherein the force measurement assembly is in the form of an instrumented treadmill.

An exemplary embodiment of a force and motion measurement system 500 having inertial compensation is depicted in FIG. 11. As shown in this figure, a subject 502 is provided with a plurality of markers 504 disposed thereon. These markers 504 are used to record the position of the limbs of the subject in 3-dimensional space. A plurality of cameras 506 are disposed in the room, and are used to track the position of the markers as the subject moves his or her limbs in 3-dimensional space. While three (3) cameras are depicted in FIG. 11, one of ordinary skill in the art will appreciate that more or less cameras can be utilized, provided that at least two cameras 506 are used. In a preferred embodiment of the invention, the subject has a plurality of single markers applied to anatomical landmarks (e.g., the iliac spines of the pelvis, the malleoli of the ankle, and the condyles of the knee), or clusters of markers applied to the middle of body segments. As the subject walks on the treadmill, the data acquisition/data processing device 104 calculates the trajectory of each marker in three (3) dimensions. Then, once the positional data is obtained using the motion acquisition/capture system, inverse kinematics are employed in order to determine the joint angles of the subject.

While the motion measurement system described above employs a plurality of markers 504, it is to be understood that the invention is not so limited. Rather, in another embodiment of the invention, a markerless motion capture system is utilized. The markerless motion capture system uses a plurality of high speed video cameras to record the motion of a subject without requiring any markers to be placed on the subject.

Figure 12:
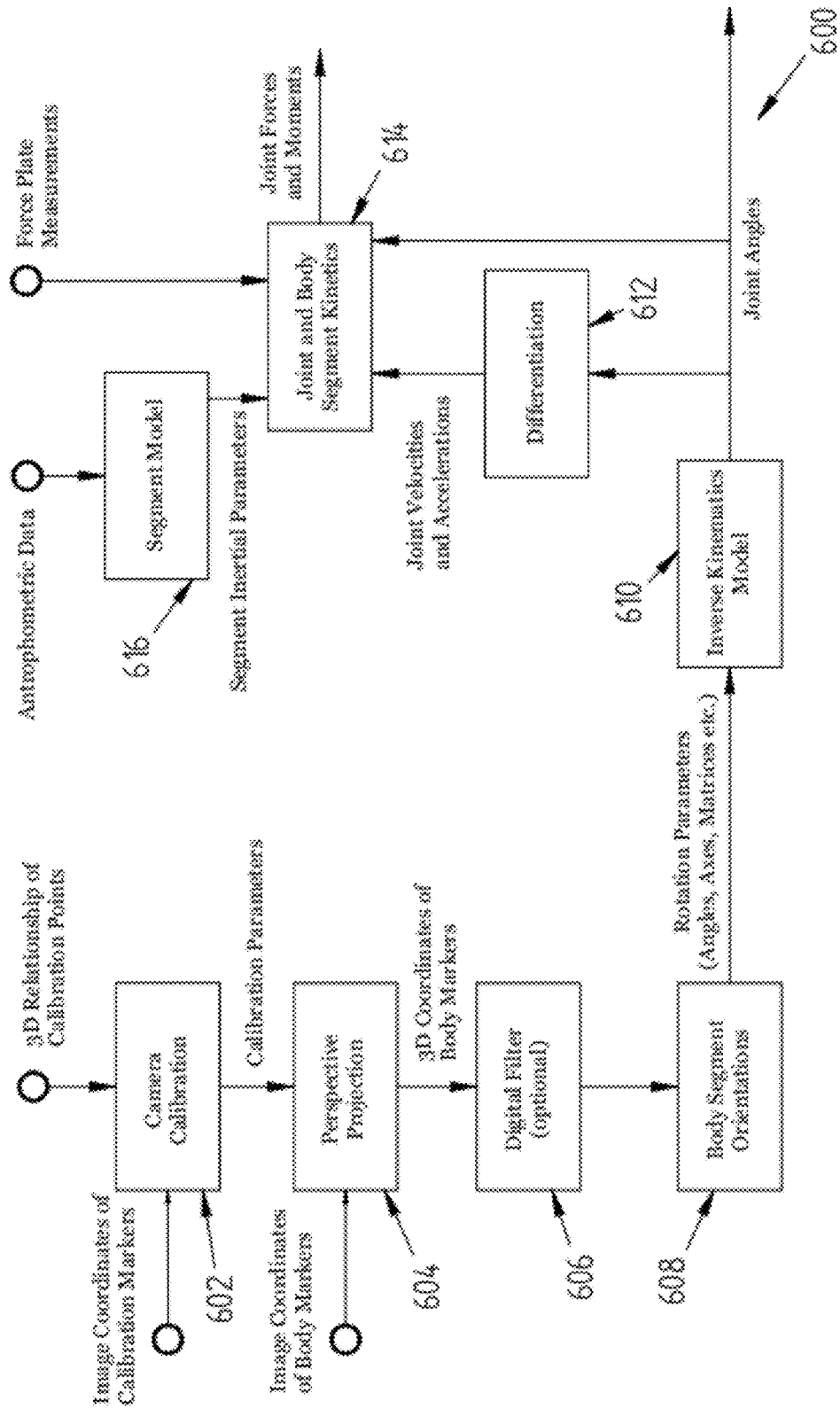
FIG. 12 is a block diagram illustrating a calculation procedure for the joint angles, velocities, and accelerations, and a calculation procedure for the joint forces and moments, both of which are carried out by the force and motion measurement system according to an embodiment of the invention.

FIG. 12 diagrammatically illustrates an exemplary calculation procedure 600 for the joint angles, velocities, and accelerations carried out by the force and motion measurement system 500 depicted in FIG. 11. Initially, as shown in block 602 of FIG. 12, the plurality of cameras 506 are calibrated using the image coordinates of calibration markers and the three-dimensional (3-D) relationship of calibration points such that a plurality of calibration parameters are generated. In one exemplary embodiment of the invention, the calibration of the plurality of cameras 506 is performed using a Direct Linear Transformation ("DLT") technique and yields eleven (11) DLT parameters. However, it is to be understood that, in other embodiments of the invention, a different technique can be used to calibrate the plurality of cameras 506. Then, in block 604, the perspective projection of the image coordinates of the body markers 504 is performed using the calibration parameters so that the image coordinates are transformed into actual three-dimensional (3-D) coordinates of the body markers 504. Because the digitization of the marker images involves a certain amount of random error, a digital filter is preferably applied to the three-dimensional (3-D) coordinates of the markers to remove the inherent noise in block 606. Although, it is to be understood that the use of a digital filter is optional, and thus is omitted in some embodiments of the invention. In block 608, local coordinate systems are utilized to determine the orientation of the body segments relative to each other. After which, in block 610, rotational parameters (e.g., angles, axes, matrices, etc.) and the inverse kinematics model are used to determine the joint angles. The inverse kinematics model contains the details of how the angles are defined, such as the underlying assumptions that are made regarding the movement of the segments relative to each other. For example, in the inverse kinematics model, the hip joint could be modeled as three separate revolute joints acting in the frontal, horizontal, and sagittal plane, respectively. In block 612, differentiation is used to determine the joint velocities and accelerations from the joint angles. Although, one of ordinary skill in the art will appreciate that, in other embodiments of the invention, both differentiation and analytical curve fitting could be used to determine the joint velocities and accelerations from the joint angles.

In addition, FIG. 12 diagrammatically illustrates the calculation procedure for the joint forces and moments that is also carried out by the force and motion measurement system 500 of FIG. 11. Referring again to this figure, anthropometric data is applied to a segment model in block 616 in order to determine the segment inertial parameters. By using the segment inertial parameters together with the joint velocities and accelerations and the force plate measurements, joint and body segment kinetics are used in block 614 to determine the desired joint forces and moments. In a preferred embodiment of the invention, Newton-Euler Formulations are used to compute the joint forces and moments. However, it is to be understood that the invention is not so limited. Rather, in other embodiments of the invention, the kinetics analysis could be carried out using a different series of equations. In order to more clearly illustrate the requisite calculations for determining the joint forces and moments, the determination of the joint reaction forces and joint moments of the subject will be explained using an exemplary joint of the body.

In particular, the computation of the joint reaction forces and joint moments of the subject will be described in reference to an exemplary determination of the forces and moments acting on the ankle. The force measurement assembly 102, 202 is used to determine the ground reaction forces and moments associated with the subject being measured. These ground reaction forces and moments are used in conjunction with the joint angles computed from the inverse kinematics analysis in order to determine the net joint reaction forces and net joint moments of the subject. In particular, inverse dynamics is used to calculate the net joint reaction forces and net joint moments of the subject by using the computed joint angles, angular velocities, and angular accelerations of a musculoskeletal model, together with the ground reaction forces and moments measured by the force measurement assembly 102, 202.

Figure 13:
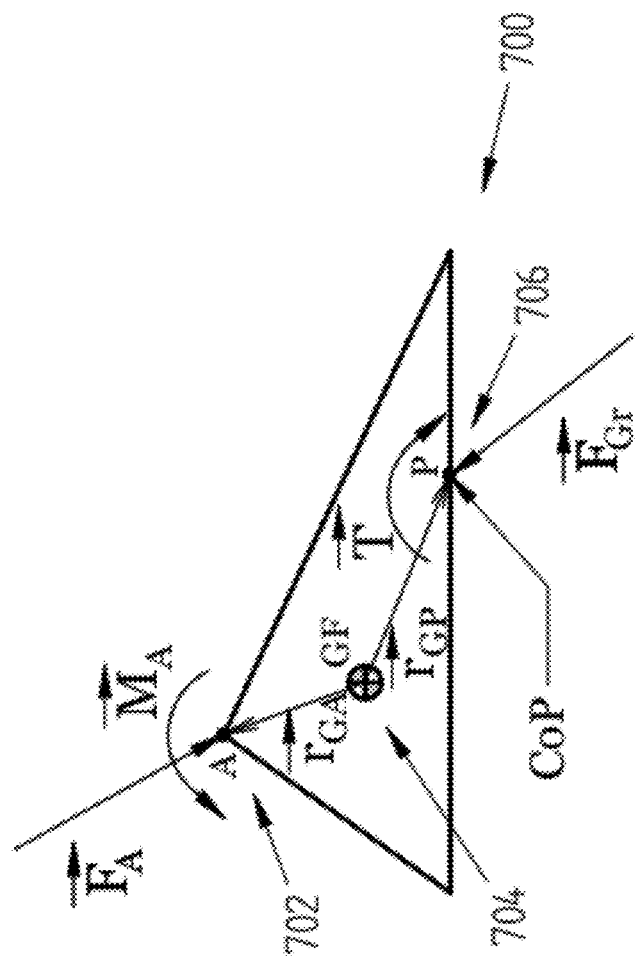
FIG. 13 is a free body diagram that diagrammatically represents the forces and moments acting on the ankle joint according to an exemplary embodiment of the invention.

An exemplary calculation of the forces and moments at the ankle joint will be explained with reference to the free body diagram 700 depicted in FIG. 13. In FIG. 13, the ankle joint 702 is diagrammatically represented by the point "A", whereas the gravitational center 704 of the foot is diagrammatically represented by the circular marker labeled "GF". In this figure, the point of application for the ground reaction forces $\vec{F}_{Gr}$ (i.e., the center of pressure 706) is diagrammatically represented by the point "P" in the free body diagram 700. The force balance equation and the moment balance equation for the ankle are as follows:

$$m_F \cdot \vec{a}_{GF} = \vec{F}_{Gr} + \vec{F}_A \tag{8}$$

$$\vec{J}_F \dot{\vec{\omega}}_F + \vec{\omega}_F \times \vec{J}_F \vec{\omega}_F = \vec{M}_A + \vec{T} + (\vec{r}_{GA} \times \vec{F}_A) + (\vec{r}_{GP} \times \vec{F}_{Gr}) \tag{9}$$

where:
  $m_F$: mass of the foot
  $\vec{a}_{GF}$: acceleration of the gravitational center of the foot
  $\vec{F}_{Gr}$: ground reaction forces
  $\vec{F}_A$: forces acting on the ankle
  $\vec{J}_F$: rotational inertia of the foot
  $\dot{\vec{\omega}}_F$: angular acceleration of the foot
  $\vec{\omega}_F$: angular velocity of the foot
  $\vec{M}_A$: moments acting on the ankle
  $\vec{T}$: torque acting on the foot
  $\vec{r}_{GA}$: position vector from the gravitational center of the foot to the center of the ankle $\vec{r}_{GP}$: position vector from the gravitational center of the foot to the center of pressure.

In above equations (8) and (9), the ground reaction forces $\vec{F}_{Gr}$ are equal in magnitude and opposite in direction to the externally applied forces $\vec{F}_e$ that the body exerts on the supporting surface through the foot (i.e., $\vec{F}_{Gr}=-\vec{F}_e$). Because the externally applied forces $\vec{F}_e$ are inertially-compensated in the manner described above prior to being utilized in equations (8) and (9), the ground reaction forces $\vec{F}_{Gr}$ have already been corrected for the errors resulting from the movement of the force measurement assembly 102, 202.

Then, in order to solve for the desired ankle forces and moments, the terms of equations (8) and (9) are rearranged as follows:

$$\vec{F}_A = m_F \vec{a}_{GF} - \vec{F}_{Gr} \qquad (10)$$

$$\vec{M}_A = \breve{J}_F \vec{\omega}_F + \vec{\omega}_F \times \breve{J}_F \vec{\omega}_F - \vec{T} - (\vec{r}_{GA} \times \vec{F}_A) - (\vec{r}_{GP} \times \vec{F}_{Gr}) \qquad (11)$$

By using the above equations, the magnitude and directions of the ankle forces and moments can be determined. The net joint reaction forces and moments for the other joints in the body can be computed in a similar manner.

Although the invention has been shown and described with respect to a certain embodiment or embodiments, it is apparent that this invention can be embodied in many different forms and that many other modifications and variations are possible without departing from the spirit and scope of this invention. For example, rather than using three 3-component accelerometers, a total of nine single-component accelerometers could be used for determining the accelerations of the force measurement assemblies 102, 202. Similarly, three single-component angular velocity sensors (rate gyroscopes) could be substituted for the single 3-component angular velocity sensor that is used in the preferred embodiment described above.

While exemplary embodiments have been described herein, one of ordinary skill in the art will readily appreciate that the exemplary embodiments set forth above are merely illustrative in nature and should not be construed as to limit the claims in any manner Rather, the scope of the invention is defined only by the appended claims and their equivalents, and not, by the preceding description.

The invention claimed is:

1. A force measurement system having inertial compensation, the force measurement system comprising:
 a force measurement assembly configured to receive a subject, the force measurement assembly including:
  a surface for receiving at least one portion of the body of the subject;
  at least one force transducer, the at least one force transducer configured to sense one or more measured quantities and output one or more signals that are representative of forces and/or moments being applied to the surface of the force measurement assembly by the subject;
 a motion base, which includes at least one actuator and a movable surface, the movable surface of the motion base attached to the force measurement assembly, the motion base configured to selectively displace and rotate its movable surface and the force measurement assembly attached thereto in multiple dimensions;
 an inertial compensation system operatively coupled to the force measurement assembly, the inertial compensation system configured to determine both multi-dimensional inertial forces and moments resulting from the displacement and rotation of the force measurement assembly by the motion base in multiple dimensions, wherein the inertial compensation system utilizes a plurality of inertial parameters, which include the mass of the force measurement assembly, for determining the multi-dimensional inertial forces and moments resulting from the displacement and rotation of the force measurement assembly in multiple dimensions by the motion base, and wherein the motion base is used for determining the plurality of inertial parameters of the force measurement assembly during a calibration procedure, the mass of the force measurement assembly being computed as a function of measured forces determined using the at least one force transducer and an acceleration of the force measurement assembly measured by at least one accelerometer of the inertial compensation system; and
 a data manipulation means configured to convert the one or more signals that are representative of the forces and/or moments being applied to the surface of the force measurement assembly by the subject into output forces and/or moments, the data manipulation means being further configured to correct the output forces and/or moments by utilizing the multi-dimensional inertial forces and/or moments determined by the inertial compensation system so as to improve the measurement accuracy of the forces and/or moments being applied to the surface of the force measurement assembly by the subject.

2. The force measurement system according to claim 1, wherein the inertial parameters further include the rotational inertia parameters of the force measurement assembly and the position of the center of gravity of the force measurement assembly.

3. The force measurement system according to claim 1, wherein the inertial compensation system comprises at least one angular velocity sensor, and wherein a multi-component angular velocity of the force measurement assembly, as measured by the at least one angular velocity sensor, is used for computing the multi-dimensional inertial moments about at least two orthogonal axes.

4. The force measurement system according to claim 1, wherein the motion base applies linear and/or rotational motion profiles to the force measurement assembly during the calibration procedure.

5. The force measurement system according to claim 1, wherein the force measurement assembly is in the form of a force plate or platform.

6. The force measurement system according to claim 1, wherein the force measurement assembly is in the form of an instrumented treadmill.

7. The force measurement system according to claim 6, wherein a force plate is disposed underneath a treadmill belt.

8. A method for accurately determining the forces and/or moments applied to a surface of a force measurement device by a subject disposed thereon, the method comprising the steps of:
 providing a force measurement assembly configured to receive a subject thereon, the force measurement assembly including:
  a surface for receiving at least one portion of the body of the subject;
  at least one force transducer, the at least one force transducer configured to sense one or more measured quantities and output one or more signals that are representative of forces and/or moments being applied to the surface of the force measurement assembly by the subject;

providing a motion base, which includes at least one actuator, operatively coupled to the force measurement assembly, the motion base configured to selectively displace and rotate the force measurement assembly in multiple dimensions;

providing an inertial compensation system operatively coupled to the force measurement assembly, the inertial compensation system configured to determine multi-dimensional inertial forces and/or moments resulting from the displacement and rotation of the force measurement assembly in multiple dimensions;

determining a plurality of inertial parameters for the force measurement assembly during a calibration procedure, the plurality of inertial parameters including the mass of the force measurement assembly, the mass of the force measurement assembly being computed as a function of measured forces determined using the at least one force transducer and an acceleration of the force measurement assembly measured by at least one accelerometer of the inertial compensation system;

positioning the subject on the surface of the force measurement assembly;

selectively displacing and rotating the force measurement assembly and the subject disposed thereon in multiple dimensions using the motion base;

determining, by using the inertial compensation system, both the multi-dimensional inertial forces and moments resulting from the multi-dimensional displacement and rotation of the force measurement assembly by the motion base;

utilizing the plurality of inertial parameters in determining the multi-dimensional inertial forces and moments resulting from the displacement and rotation of the force measurement assembly in multiple dimensions by the motion base;

sensing, by utilizing the at least one force transducer, one or more measured quantities that are representative of forces and/or moments being applied to the surface of the force measurement assembly by the subject and outputting one or more signals representative thereof;

converting, by using a data manipulation device, the one or more signals that are representative of the forces and/or moments being applied to the surface of the force measurement assembly by the subject into output forces and/or moments; and correcting the output forces and/or moments by mathematically combining the output forces and/or moments with the multi-dimensional inertial forces and/or moments determined by the inertial compensation system so as to improve the measurement accuracy of the forces and/or moments being applied to the surface of the force measurement assembly by the subject.

9. The method according to claim 8, wherein the inertial parameters further include the rotational inertia parameters of the force measurement assembly and the position of the center of gravity of the force measurement assembly.

10. The method according to claim 8, further comprising the step of:
using the motion base to determine the plurality of inertial parameters of the force measurement assembly during the calibration procedure.

11. The method according to claim 10, further comprising the step of:

applying linear and/or rotational motion profiles to the force measurement assembly during the calibration procedure by using the motion base.

12. A force and/or motion measurement system with inertial compensation, comprising:
a motion acquisition system having a plurality of motion sensing devices configured to capture the movement of a plurality of limbs on a subject, the motion sensing devices generating a plurality of first measured quantities;
a force measurement assembly configured to receive the subject, the force measurement assembly including:
a surface for receiving at least one portion of the body of the subject;
at least one force transducer, the at least one force transducer configured to sense one or more second measured quantities and output one or more signals that are representative of forces and/or moments being applied to the surface of the force measurement assembly by the subject;
a motion base, which includes at least one actuator, operatively coupled to the force measurement assembly, the motion base configured to selectively displace and rotate the force measurement assembly in multiple dimensions;
an inertial compensation system operatively coupled to the force measurement assembly, the inertial compensation system configured to determine both multi-dimensional inertial forces and moments resulting from the displacement and rotation of the force measurement assembly by the motion base in multiple dimensions, wherein the inertial compensation system utilizes a plurality of inertial parameters, which include the mass of the force measurement assembly, for determining the multi-dimensional inertial forces and moments resulting from the displacement and rotation of the force measurement assembly in multiple dimensions by the motion base, and wherein the motion base is used for determining the plurality of inertial parameters of the force measurement assembly during a calibration procedure, the mass of the force measurement assembly being computed as a function of measured forces determined using the at least one force transducer and an acceleration of the force measurement assembly measured by at least one accelerometer of the inertial compensation system; and
a data manipulation means being configured to convert the one or more signals that are representative of the forces and/or moments being applied to the surface of the force measurement assembly by the subject into output forces and/or moments, the data manipulation means being further configured to correct the output forces and/or moments by utilizing the multi-dimensional inertial forces and/or moments determined by the inertial compensation system, and the data manipulation means being additionally configured to determine forces and/or moments at one or more joints of the subject by using the corrected output forces and/or moments in combination with force and/or moment data generated from the plurality of first measured quantities.

13. The force and/or motion measurement system according to claim 12, wherein the inertial parameters further include the rotational inertia parameters of the force measurement assembly and the position of the center of gravity of the force measurement assembly.

14. The force and/or motion measurement system according to claim 12, wherein the inertial compensation system comprises at least one angular velocity sensor, and wherein a multi-component angular velocity of the force measurement assembly, as measured by the at least one angular velocity sensor, is used for computing the multi-dimensional inertial moments about at least two orthogonal axes.

15. The force and/or motion measurement system according to claim 12, wherein the motion base applies linear and/or rotational motion profiles to the force measurement assembly during the calibration procedure.

16. The force and/or motion measurement system according to claim 12, wherein the force measurement assembly is in the form of a force plate or platform.

17. The force and/or motion measurement system according to claim 12, wherein the force measurement assembly is in the form of an instrumented treadmill.

18. The force and/or motion measurement system according to claim 17, wherein a force plate is disposed underneath a treadmill belt.

* * * * *